(12) United States Patent
Qin et al.

(10) Patent No.: US 12,291,819 B2
(45) Date of Patent: May 6, 2025

(54) ZONED AND/OR LAYERED SUBSTRATES AND METHOD AND APPARATUS FOR PRODUCING THE SAME

(71) Applicant: KIMBERLY-CLARK WORLDWIDE, INC., Neenah, WI (US)

(72) Inventors: Jian Qin, Appleton, WI (US); Sridhar Ranganathan, Alpharetta, GA (US); Francis P. Abuto, Johns Creek, GA (US); Vikram Kaul, Atlanta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 211 days.

(21) Appl. No.: 17/915,833

(22) PCT Filed: Mar. 31, 2021

(86) PCT No.: PCT/US2021/025049
§ 371 (c)(1),
(2) Date: Sep. 29, 2022

(87) PCT Pub. No.: WO2021/202640
PCT Pub. Date: Oct. 7, 2021

(65) Prior Publication Data
US 2023/0131582 A1    Apr. 27, 2023

Related U.S. Application Data

(60) Provisional application No. 63/002,570, filed on Sep. 29, 2022.

(51) Int. Cl.
| | |
|---|---|
| *D04H 1/4374* | (2012.01) |
| *A61F 13/53* | (2006.01) |
| *D04H 1/407* | (2012.01) |
| *D04H 1/425* | (2012.01) |
| *D04H 1/4382* | (2012.01) |
| *D04H 1/541* | (2012.01) |
| *D04H 1/544* | (2012.01) |
| *D04H 1/55* | (2012.01) |
| *D04H 1/732* | (2012.01) |
| *D21F 1/02* | (2006.01) |
| *D21F 11/00* | (2006.01) |
| *A61F 13/15* | (2006.01) |
| *A61F 13/537* | (2006.01) |

(52) U.S. Cl.
CPC ............ *D21F 11/002* (2013.01); *A61F 13/53* (2013.01); *D04H 1/407* (2013.01); *D04H 1/425* (2013.01); *D04H 1/4374* (2013.01); *D04H 1/43835* (2020.05); *D04H 1/5412* (2020.05); *D04H 1/544* (2013.01); *D04H 1/55* (2013.01); *D04H 1/732* (2013.01); *D21F 1/022* (2013.01); *A61F 13/15699* (2013.01); *A61F 13/53717* (2013.01); *D10B 2509/026* (2013.01)

(58) Field of Classification Search
CPC ........ D21H 11/00; D21H 13/00; D21H 17/00; D21H 17/03; D21H 17/33; D21H 17/53; D21H 17/63; D21H 21/24; D21H 27/00; D21H 27/30; D21F 11/002; D21F 1/022; D21F 11/04; D04H 1/407; D04H 1/425; D04H 1/4374; D04H 1/43835; D04H 1/5412; D04H 1/544; D04H 1/55; D04H 1/732; D04H 1/26; D04H 1/43916; D04H 1/736; A61F 13/53; A61F 13/15699; A61F 13/53717; B32B 29/00; B32B 29/005; D10B 2509/026
See application file for complete search history.

(56) References Cited

U.S. PATENT DOCUMENTS

| | | | |
|---|---|---|---|
| 3,843,470 A | 10/1974 | Betley et al. | |
| 3,846,229 A | 11/1974 | Kallmes | |
| 4,604,164 A | 8/1986 | Fujiwara et al. | |
| 4,812,208 A | 3/1989 | Yuasa et al. | |
| 5,603,807 A | 2/1997 | Heinzmann | |
| 5,820,734 A | 10/1998 | Pantaleo et al. | |
| 5,849,159 A | 12/1998 | Heinzmann et al. | |
| 5,853,281 A | 12/1998 | Farmer | |
| 6,518,479 B1 | 2/2003 | Graef et al. | |

(Continued)

FOREIGN PATENT DOCUMENTS

| | | | | |
|---|---|---|---|---|
| EP | 1071388 B1 | * | 9/2002 | ....... A61F 13/15617 |
| GB | 2058865 A | | 4/1981 | |

(Continued)

OTHER PUBLICATIONS

Dutkiewicz, Jacek, "Some Advances in Nonwoven Structures for Absorbency, Comfort and Aesthetics", AUTEXRJ.com, Sep. 2002, http://www.autexrj.com/cms/zalaczone_pliki/6-02-3.pdf.

*Primary Examiner* — Jose A Fortuna

(74) *Attorney, Agent, or Firm* — KIMBERLY-CLARK WORLDWIDE, INC.

(57) ABSTRACT

Methods and apparatuses for producing a zoned and/or layered substrate are described. A substrate can include a first layer including a first zone, a second zone, and an interface between zones. The first zone can include a plurality of fibers. The second zone can include a plurality of fibers and can be offset from the first zone in a cross-direction. The interface can include at least some of the plurality of fibers of the first zone and at least some of the plurality of fibers of the second zone to provide a purity gradient with a transition width less than 3.8 cm as defined by the Purity Gradient Test Method as described herein.

20 Claims, 10 Drawing Sheets

(56) References Cited

U.S. PATENT DOCUMENTS

| | | |
|---|---|---|
| 6,765,125 B2 | 7/2004 | Abuto |
| 7,067,040 B2 | 6/2006 | Lepomaki et al. |
| 7,166,190 B2 | 1/2007 | Graef et al. |
| 8,461,412 B2 | 6/2013 | Febo et al. |
| 9,161,869 B2 | 10/2015 | Lee et al. |
| 9,422,665 B2 | 8/2016 | Ewald |
| 11,866,884 B2 * | 1/2024 | Qin .................. D04H 1/5412 |
| 2003/0018311 A1 | 1/2003 | Graef et al. |
| 2006/0005934 A1 | 1/2006 | Graef et al. |
| 2012/0173249 A1 | 7/2012 | Popp et al. |
| 2016/0229088 A1 | 8/2016 | Ojala et al. |
| 2018/0353350 A1 | 12/2018 | Lee et al. |
| 2023/0131582 A1 * | 4/2023 | Qin .................... D04H 1/732 |
| | | 428/213 |
| 2023/0149226 A1 * | 5/2023 | Qin .................... D04H 1/736 |
| | | 604/378 |
| 2024/0125048 A1 * | 4/2024 | Qin ................. D04H 1/43835 |

FOREIGN PATENT DOCUMENTS

| | | | | |
|---|---|---|---|---|
| WO | 1999045194 A1 | 9/1999 | | |
| WO | 1999047590 A1 | 9/1999 | | |
| WO | WO-9947590 A1 * | 9/1999 | ......... | A61F 13/5146 |
| WO | 2008082546 A1 | 7/2008 | | |
| WO | 2021202637 A1 | 3/2020 | | |
| WO | WO-2022093886 A1 * | 5/2022 | ............. | A61F 13/53 |
| WO | WO-2024107669 A1 * | 5/2024 | ....... | A61F 13/15203 |

\* cited by examiner

ZONED AND/OR LAYERED SUBSTRATES AND METHOD AND APPARATUS FOR PRODUCING THE SAME

TECHNICAL FIELD

The present disclosure relates to methods and apparatuses that can produce a zoned and/or layered substrate and such substrates. More specifically, the present disclosure relates to foam-forming methods and headboxes that can produce a zoned and/or layered substrate and such substrates.

BACKGROUND OF THE DISCLOSURE

Current commercial personal care products, such as diapers, diaper pants, training pants, and adult incontinence products, typically include different components to provide an absorbent structure that are each typically prepared from different processing lines using different raw materials. Each component, such as the acquisition material (or surge), absorbent core, and core wrap (or distribution layer) performs well for its designed purposes. However, the compilation of each component on a commercial manufacturing line requires that these separate materials be bonded to one another, such as through the use of adhesives. The bonding interface can inhibit performance properties of the overall structure in comparison to its designed function and performance. For example, an adhesive interface between components in an absorbent composite can resist body fluid penetrating from one component to the other, which can provide a negative impact on fluid intake and distribution properties of an absorbent product. Not only can such an adhesive interface reduce fluid handling properties of specific structures within an absorbent composite, but it can also it negatively affect dry product properties, such as softness, flexibility, comfort and fit, etc. Similar issues can exist for layered or zoned products, for example, such as, tissues, wipes, and/or wipers. For example, adhesive bonding between adjacent plies in a tissue product can reduce softness of the tissue product. Thermal bonding and/or pressure bonding are two other techniques that can be used to combine two separate materials at discrete points. While such methods may not reduce softness as much adhesive bonding of separate components, such bonding techniques may still provide some negative impact on fluid handling properties at such bonded locations.

In addition, current manufacturing practices of creating separate components for an absorbent composite often do not provide the flexibility to provide zoned structural components that can provide enhanced performance within an absorbent structure and higher raw material efficiency or do not provide adequate control over the gradient between adjacent zones of a zoned substrate.

Thus, there exists a need to develop a method and apparatus for creating a zoned and/or layered substrate. There is also a need to develop a method and apparatus for creating a zoned substrate that can provide enhanced control of the gradient between adjacent zones of a zoned substrate. There is also a need to develop multi-layered structures without the use of adhesive materials between the layers and that can control the gradient between adjacent layers. There is also a need to develop multi-layered structures that include zoned substrates without the use of adhesive materials between the layers.

SUMMARY OF THE DISCLOSURE

In one embodiment, a substrate is provided. The substrate can include a machine direction, a cross-direction, and a z-direction perpendicular to a plane defined by the machine direction and the cross-direction. The substrate can include a first layer. The first layer can include a first zone including a plurality of fibers. The first layer can also include a second zone including a plurality of fibers. The second zone can be offset from the first zone in the cross-direction. The first layer can additionally include an interface between the first zone and the second zone. The interface between the first zone and the second zone can include at least some of the plurality of fibers of the first zone being mixed with at least some of the plurality of fibers of the second zone to provide a purity gradient with a transition width less than 3.8 cm as defined by a Purity Gradient Test Method as described herein.

In another embodiment, a substrate is provided. The substrate can include a machine direction, a cross-direction, and a z-direction perpendicular to a plane defined by the machine direction and the cross-direction. The substrate can include a first layer. The first layer can include a first zone including a plurality of fibers. The first layer can also include a second zone including a plurality of fibers. The second zone can be offset from the first zone in the cross-direction. The first layer can additionally include an interface between the first zone and the second zone. The interface between the first zone and the second zone can include at least some of the plurality of fibers of the first zone being mixed with at least some of the plurality of fibers of the second zone to provide a purity gradient with a transition slope greater than 28 gray/cm as defined by a Purity Gradient Test Method as described herein.

In still another embodiment, a substrate is provided. The substrate can include a machine direction, a cross-direction, and a z-direction perpendicular to a plane defined by the machine direction and the cross-direction. The substrate can include a first layer. The first layer can include a first zone including a plurality of fibers. The substrate can include a second layer. The second layer can be offset from the first layer in the z-direction. The second layer can include a second zone comprising a plurality of superabsorbent material particles. The substrate can also include an interface between the first layer and the second layer. The interface between the first layer and the second layer can include at least some of the plurality of fibers of the first zone of the first layer being mixed with at least some of the plurality of superabsorbent material particles of the second zone of the second layer. The superabsorbent material particles of the second layer are controlled such that a relative thickness of the second layer is less than 70% of a total thickness of the substrate as measured by the Layer Relative Thickness Test as described herein.

BRIEF DESCRIPTION OF THE DRAWINGS

A full and enabling disclosure thereof, directed to one of ordinary skill in the art, is set forth more particularly in the remainder of the specification, which makes reference to the appended figures in which.

DETAILED DESCRIPTION OF THE DISCLOSURE

Figure 1:
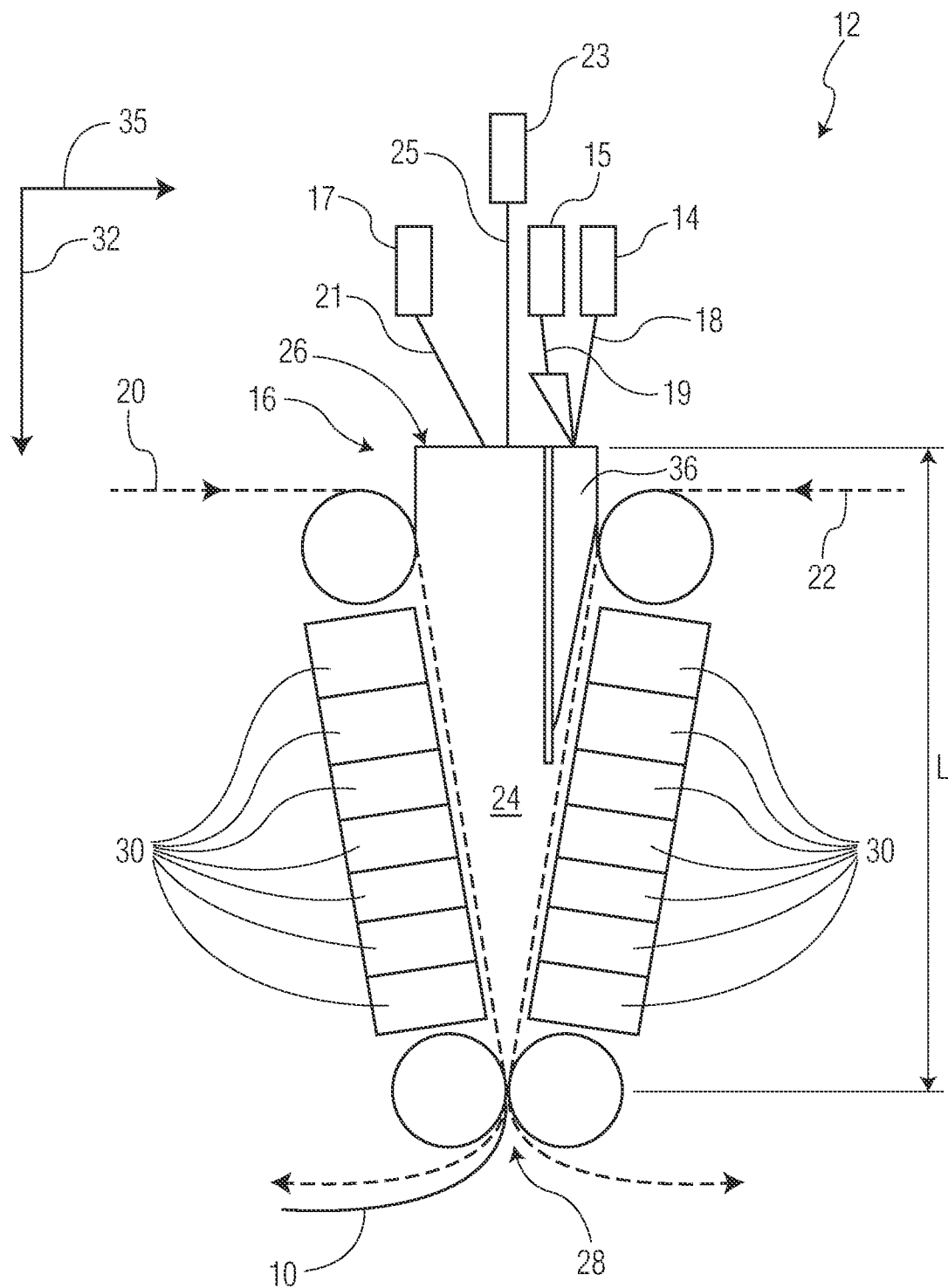
FIG. 1 is a side plan view of an exemplary headbox including a divider that can provide a zoned substrate of the present disclosure.

The present disclosure is directed to methods and apparatuses that can produce a zoned and/or layered substrate and such substrates. While the present disclosure provides examples of zoned and/or layered substrates manufactured through foam-forming, it is contemplated that the methods and apparatuses described herein may be utilized to benefit wet-laid and/or air-laid manufacturing processes.

Each example is provided by way of explanation and is not meant as a limitation. For example, features illustrated or described as part of one embodiment or figure can be used on another embodiment or figure to yield yet another embodiment. It is intended that the present disclosure include such modifications and variations.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. As used herein, the terminology of "first," "second," "third", etc. does not designate a specified order, but is used as a means to differentiate between different occurrences when referring to various features in the present disclosure. Many modifications and variations of the present disclosure can be made without departing from the spirit and scope thereof. Therefore, the exemplary embodiments described herein should not be used to limit the scope of the invention.

Definitions

As used herein, the term "foam formed product" means a product formed from a suspension including a mixture of a solid, a liquid, and dispersed gas bubbles.

As used herein, the term "foam forming process" means a process for manufacturing a product involving a suspension including a mixture of a solid, a liquid, and dispersed gas bubbles.

As used herein, the term "foaming fluid" means any one or more known fluids compatible with the other components in the foam forming process. Suitable foaming fluids include, but are not limited to, water.

As used herein, the term "foam half life" means the time elapsed until the half of the initial frothed foam mass reverts to liquid water.

As used herein, the term "layer" refers to a structure that provides an area of a substrate in a z-direction of the substrate that is comprised of similar components and structure.

As used herein, the term "nonwoven web" means a web having a structure of individual fibers or threads which are interlaid, but not in an identifiable manner as in a knitted web.

As used herein, unless expressly indicated otherwise, when used in relation to material compositions the terms "percent", "%", "weight percent", or "percent by weight" each refer to the quantity by weight of a component as a percentage of the total except as whether expressly noted otherwise.

The term "personal care absorbent article" refers herein to an article intended and/or adapted to be placed against or in proximity to the body (i.e., contiguous with the body) of the wearer to absorb and contain various liquid, solid, and semi-solid exudates discharged from the body. Examples include, but are not limited to, diapers, diaper pants, training pants, youth pants, swim pants, feminine hygiene products, including, but not limited to, menstrual pads or pants, incontinence products, medical garments, surgical pads and bandages, and so forth.

The term "ply" refers to a discrete layer within a multi-layered product wherein individual plies may be arranged in juxtaposition to each other.

The term "plied" or "bonded" or "coupled" refers herein to the joining, adhering, connecting, attaching, or the like, of two elements. Two elements will be considered plied, bonded or coupled together when they are joined, adhered, connected, attached, or the like, directly to one another or indirectly to one another, such as when each is directly bonded to intermediate elements. The plying, bonding or coupling of one element to another can occur via continuous or intermittent bonds.

The term "superabsorbent material" as used herein refers to water-swellable, water-insoluble organic or inorganic materials including superabsorbent polymers and superabsorbent polymer compositions capable, under the most favorable conditions, of absorbing at least about 10 times their weight, or at least about 15 times their weight, or at least about 25 times their weight in an aqueous solution containing 0.9 weight percent sodium chloride.

The term "zone" as used herein with respect to a substrate refers to a particular area of a substrate in the cross-direction of the substrate that is comprised of similar components and structure.

Method and Apparatus

In one embodiment, the present disclosure relates to a foam forming process and associated method that can be employed to manufacturing a zoned substrate 10, 110, 210, 310. FIG. 1 provides an exemplary apparatus 12 that can be used as part of a foam forming process to manufacture a foam formed product. The apparatus 12 of FIG. 1 can form part of a foam forming process that can include a pulper that can mix fibers, a fluid, and a surfactant, as will be discussed in greater detail below. The pulper can mix (e.g., agitates) the surfactant and the fluid (e.g., water) with air to create a foam. The pulper also mixes the foam with the fibers to create a foam suspension of fibers in which the foam holds and separates the fibers to facilitate a distribution of the fibers within the foam (e.g., as an artifact of the mixing process in the pulper). Uniform fiber distribution can promote desirable nonwoven material characteristics including, for example, strength and the visual appearance of quality.

Foaming Fluid

The foam forming processes as described herein can include a foaming fluid. In some embodiments, the foaming fluid can comprise between about 85% to about 99.99% of the foam (by weight). In some embodiments, the foaming fluid used to make the foam can comprise at least about 85% of the foam (by weight). In certain embodiments, the foaming fluid can comprise between about 90% and about 99.9% of the foam (by weight). In certain other embodiments, the foaming fluid can comprise between about 93% and 99.5% of the foam or even between about 95% and about 99.0% of the foam (by weight). In preferred embodiments, the foaming fluid can be water, however, it is contemplated that other processes may utilize other foaming fluids.

Foaming Surfactant

The foam forming processes as described herein can utilize one of more surfactants. The fibers and surfactant, together with the foaming liquid and any additional components, can form a stable dispersion capable of substantially retaining a high degree of porosity for longer than the drying process. In this regard, the surfactant is selected so as to provide a foam having a foam half life of at least 2 minutes, more desirably at least 5 minutes, and most desirably at least 10 minutes. A foam half life can be a function of surfactant types, surfactant concentrations, foam compositions/solid level and mixing power/air content in a foam. The foaming surfactant used in the foam can be selected from one or more known in the art that are capable of providing the desired degree of foam stability. In this regard, the foaming surfactant can be selected from anionic, cationic, nonionic and amphoteric surfactants provided they, alone or in combination with other components, provide the necessary foam stability, or foam half life. As will be appreciated, more than one surfactant can be used, including different types of surfactants, as long as they are compatible, and more than one surfactant of the same type. For example, a combination of a cationic surfactant and a nonionic surfactant or a combination of an anionic surfactant and a nonionic surfactant may be used in some embodiments due to their compatibilities. However, in some embodiments, a combination of a cationic surfactant and an anionic surfactant may not be satisfactory to combine due to incompatibilities between the surfactants.

Anionic surfactants believed suitable for use with the present disclosure include, without limitation, anionic sulfate surfactants, alkyl ether sulfonates, alkylaryl sulfonates, or mixtures or combinations thereof. Examples of alkylaryl sulfonates include, without limitation, alkyl benzene sulfonic acids and their salts, dialkylbenzene disulfonic acids and their salts, dialkylbenzene sulfonic acids and their salts, alkylphenol sulfonic acids/condensed alkylphenol sulfonic acids and their salts, or mixture or combinations thereof. Examples of additional anionic surfactants believed suitable for use in the present disclosure include alkali metal sulforicinates, sulfonated glyceryl esters of fatty acids such as sulfonated monoglycerides of coconut oil acids, salts of sulfonated monovalent alcohol esters such as sodium oleylisethianate, metal soaps of fatty acids, amides of amino sulfonic acids such as the sodium salt of oleyl methyl tauride, sulfonated products of fatty acids nitriles such as palmitonitrile sulfonate, alkali metal alkyl sulfates such as sodium lauryl sulfate, ammonium lauryl sulfate or triethanolamine lauryl sulfate, ether sulfates having alkyl groups of 8 or more carbon atoms such as sodium lauryl ether sulfate, ammonium lauryl ether sulfate, sodium alkyl aryl ether sulfates, and ammonium alkyl aryl ether sulfates, sulphuric esters of polyoxyethylene alkyl ether, sodium salts, potassium salts, and amine salts of alkylnapthylsulfonic acid. Certain phosphate surfactants including phosphate esters such as sodium lauryl phosphate esters or those available from the Dow Chemical Company under the tradename TRITON are also believed suitable for use herewith. A particularly desired anionic surfactant is sodium dodecyl sulfate (SDS).

Cationic surfactants are also believed suitable for use with the present disclosure for manufacturing some embodiments of substrates. In some embodiments, such as those including superabsorbent material, cationic surfactants may be less preferable to use due to potential interaction between the cationic surfactant(s) and the superabsorbent material, which may be anionic. Foaming cationic surfactants include, without limitation, monocarbyl ammonium salts, dicarbyl ammonium salts, tricarbyl ammonium salts, monocarbyl phosphonium salts, dicarbyl phosphonium salts, tricarbyl phosphonium salts, carbylcarboxy salts, quaternary ammonium salts, imidazolines, ethoxylated amines, quaternary phospholipids and so forth. Examples of additional cationic surfactants include various fatty acid amines and amides and their derivatives, and the salts of the fatty acid amines and amides. Examples of aliphatic fatty acid amines include dodecylamine acetate, octadecylamine acetate, and acetates of the amines of tallow fatty acids, homologues of aromatic amines having fatty acids such as dodecylanalin, fatty amides derived from aliphatic diamines such as undecylimidazoline, fatty amides derived from aliphatic diamines such as undecylimidazoline, fatty amides derived from disubstituted amines such as oleylaminodiethylamine, derivatives of ethylene diamine, quaternary ammonium compounds and their salts which are exemplified by tallow trimethyl ammonium chloride, dioctadecyldimethyl ammonium chloride, didodecyldimethyl ammonium chloride, dihexadecyl ammonium chloride, alkyltrimethylammonium hydroxides, dioctadecyldimethylammonium hydroxide, tallow trimethylammonium hydroxide, trimethylammonium hydroxide, methylpolyoxyethylene cocoammonium chloride, and dipalmityl hydroxyethylammonium methosulfate, amide derivatives of amino alcohols such as beta-hydroxylethylstearylamide, and amine salts of long chain fatty acids. Further examples of cationic surfactants believed suitable for use with the present disclosure include benzalkonium chloride, benzethonium chloride, cetrimonium bromide, distearyldimethylammonium chloride, tetramethylammonium hydroxide, and so forth.

Nonionic surfactants believed suitable for use in the present disclosure include, without limitation, condensates of ethylene oxide with a long chain fatty alcohol or fatty acid, condensates of ethylene oxide with an amine or an amide, condensation products of ethylene and propylene oxides, fatty acid alkylol amide and fatty amine oxides.

Various additional examples of non-ionic surfactants include stearyl alcohol, sorbitan monostearate, octyl glucoside, octaethylene glycol monododecyl ether, lauryl glucoside, cetyl alcohol, cocamide MEA, monolaurin, polyoxyalkylene alkyl ethers such as polyethylene glycol long chain (12-14C) alkyl ether, polyoxyalkylene sorbitan ethers, polyoxyalkylene alkoxylate esters, polyoxyalkylene alkylphenol ethers, ethylene glycol propylene glycol copolymers, polyvinyl alcohol, alkylpolysaccharides, polyethylene glycol sorbitan monooleate, octylphenol ethylene oxide, and so forth.

The foaming surfactant can be used in varying amounts as necessary to achieve the desired foam stability and air-content in the foam. In certain embodiments, the foaming surfactant can comprise between about 0.005% and about 5% of the foam (by weight). In certain embodiments the foaming surfactant can comprise between about 0.05% and about 3% of the foam or even between about 0.05% and about 2% of the foam (by weight).

Fibers

The foam suspension of fibers can provide one or more supply of fibers. In some embodiments, the fibers utilized herein can include natural fibers and/or synthetic fibers. In some embodiments, a fiber supply can include only natural fibers or only synthetic fibers. In other embodiments, a fiber supply can include a mixture of natural fibers and synthetic fibers. Some fibers being utilized herein can be absorbent, whereas other fibers utilized herein can be non-absorbent. Non-absorbent fibers can provide features for the substrates that are formed from the methods and apparatuses described herein, such as improved intake or distribution of fluids.

A wide variety of cellulosic fibers are believed suitable for use herein. In some embodiments, the fibers utilized can be conventional papermaking fibers such as wood pulp fibers formed by a variety of pulping processes, such as kraft pulp, sulfite pulp, bleached chemithermomechanical pulp (BCTMP), chemithermomechanical pulp (CTMP), pressure/pressure thermomechanical pulp (PIMP), thermomechanical pulp (TMP), thermomechanical chemical pulp (TMCP), and so forth. By way of example only, fibers and methods of making wood pulp fibers are disclosed in U.S. Pat. No. 4,793,898 to Laamanen et al.; U.S. Pat. No. 4,594,130 to Chang et al.; U.S. Pat. No. 3,585,104 to Kleinhart; U.S. Pat. No. 5,595,628 to Gordon et al.; U.S. Pat. No. 5,522,967 to Shet; and so forth. Further, the fibers may be any high-average fiber length wood pulp, low-average fiber length wood pulp, or mixtures of the same. Examples of suitable high-average length pulp fibers include softwood fibers, such as, but not limited to, northern softwood, southern softwood, redwood, red cedar, hemlock, pine (e.g., southern pines), spruce (e.g., black spruce), and the like. Examples of suitable low-average length pulp fibers include hardwood fibers, such as, but not limited to, *eucalyptus*, maple, birch, aspen, and the like.

Moreover, if desired, secondary fibers obtained from recycled materials may be used, such as fiber pulp from sources such as, for example, newsprint, reclaimed paperboard, and office waste. In a particularly preferred embodiment refined fibers are utilized in the tissue web such that the total amount of virgin and/or high average fiber length wood fibers, such as softwood fibers, may be reduced.

Regardless of the origin of the wood pulp fiber, the wood pulp fibers preferably have an average fiber length greater than about 0.2 mm and less than about 3 mm, such as from about 0.35 mm and about 2.5 mm, or between about 0.5 mm to about 2 mm or even between about 0.7 mm and about 1.5 mm.

In addition, other cellulosic fibers that can be used in the present disclosure includes nonwoody fibers. As used herein, the term "non-wood fiber" generally refers to cellulosic fibers derived from non-woody monocotyledonous or dicotyledonous plant stems. Non-limiting examples of dicotyledonous plants that may be used to yield non-wood fiber include kenaf, jute, flax, ramie and hemp. Non-limiting examples of monocotyledonous plants that may be used to yield non-wood fiber include cereal straws (wheat, rye, barley, oat, etc.), stalks (corn, cotton, sorghum, Hesperaloe funifera, etc.), canes (bamboo, sisal, bagasse, etc.) and grasses (*miscanthus*. esparto, lemon, sabai, switchgrass, etc). In still other certain instances non-wood fiber may be derived from aquatic plants such as water hyacinth, microalgae such as *Spirulina*, and macroalgae seaweeds such as red or brown algae.

Still further, other cellulosic fibers for making substrates herein can include synthetic cellulose fiber types formed by spinning, including rayon in all its varieties, and other fibers derived from viscose or chemically-modified cellulose such as, for example, those available under the trade names LYOCELL and TENCEL. Some chemically-modified cellulose fibers that can be employed in substrates described herein can include chemically crosslinked pulp fibers, such as CMC535 fibers produced by International Paper.

In some embodiments, the non-woody and synthetic cellulosic fibers can have fiber length greater than about 0.2 mm including, for example, having an average fiber size between about 0.5 mm and about 50 mm or between about 0.75 and about 30 mm or even between about 1 mm and about 25 mm. Generally speaking, when fibers of relatively larger average length are being used, it may often be advantageous to modify the amount and type of foaming surfactant. For example, in some embodiments, if fibers of relatively larger average length are being used, it may be beneficial to utilize relatively higher amounts of foaming surfactant in order to help achieve a foam with the required foam half life.

Additional fibers that may be utilized in the present disclosure include fibers that are resistant to the forming fluid, namely those that are non-absorbent and whose bending stiffness is substantially unimpacted by the presence of forming fluid. As noted above, typically the forming fluid will comprise water. By way of non-limiting example, water-resistant fibers include fibers such as polymeric fibers comprising polyolefin, polyester (PET), polyamide, polylactic acid, or other fiber forming polymers. Polyolefin fibers, such as polyethylene (PE) and polypropylene (PP), are particularly well suited for use in the present disclosure. In some embodiments, non-absorbent fibers can be recycled fibers, compostable fibers, and/or marine degradable fibers. In addition, highly cross-linked cellulosic fibers having no-significant absorbent properties can also be used herein. In this regard, due to its very low levels of absorbency to water, water resistant fibers do not experience a significant change in bending stiffness upon contacting an aqueous fluid and therefore are capable of maintain an open composite structure upon wetting. The fiber composition and diameter of a fiber can contribute to enhanced bending stiffness. For example, a PET fiber has a higher bending stiffness than a polyolefin fiber whether in dry or wet states due to composition. The higher the fiber diameter, the higher the bending stiffness a fiber exhibits. Water resistant fibers desirably have a water retention value (WRV) less than about 1 and still more desirably between about 0 and about 0.5. In certain aspects, it is desirable that the fibers, or at least a portion thereof, include non-absorbent fibers.

The synthetic and/or water resistant fibers can have fiber length greater than about 0.2 mm including, for example, having an average fiber size between about 0.5 mm and about 50 mm or between about 0.75 and about 30 mm or even between about 1 mm and about 25 mm.

In some embodiments, the synthetic and/or water resistant fibers can have a crimped structure to enhance bulk generation capability of the foam formed fibrous substrate. For example, a PET crimped staple fiber may be able to generate a higher caliper (or result in a low sheet density) in comparison to a PET straight staple fiber with the same fiber diameter and fiber length.

In some embodiments, the total content of fibers, can comprise between about 0.01% to about 10% of the foam (by weight), and in some embodiments between about 0.1% to about 5% of the foam (by weight).

Binder

In some embodiments, a foam as provided herein can include binder materials. Binder materials that may be used in the present disclosure can include, but are not limited to, thermoplastic binder fibers, such as PET/PE bicomponent binder fiber, and water-compatible adhesives such as, for example, latexes. In some embodiments, binder materials as used herein can be in powder form, for example, such as thermoplastic PE powder. Importantly, the binder can comprise one that is water insoluble on the dried substrate. In certain embodiments, latexes used in the present disclosure can be cationic or anionic to facilitate application to and adherence to cellulosic fibers that can be used herein. For instance, latexes believed suitable for use include, but are not limited to, anionic styrene-butadiene copolymers, polyvinyl acetate homopolymers, vinyl-acetate ethylene copolymers, vinyl-acetate acrylic copolymers, ethylene-vinyl chloride copolymers, ethylene-vinyl chloride-vinyl acetate terpolymers, acrylic polyvinyl chloride polymers, acrylic polymers, nitrile polymers, as well as other suitable anionic latex polymers known in the art. Examples of such latexes are described in U.S. Pat. No. 4,785,030 to Hager, U.S. Pat. No. 6,462,159 to Hamada, U.S. Pat. No. 6,752,905 to Chuang et al. and so forth. Examples of suitable thermoplastic binder fibers include, but are not limited to, monocomponent and multi-component fibers having at least one relatively low melting thermoplastic polymer such as polyethylene. In certain embodiments, polyethylene/polypropylene sheath/core staple fibers can be used. Binder fibers may have lengths in line with those described herein above in relation to the synthetic cellulosic fibers.

Exemplary commercially available binder fibers include T 255 binder fiber with a 6 or 12 mm fiber length and a 2.2 dtex fiber diameter from Trevia or WL Adhesion C binder fiber with a 4 mm fiber length and a 1.7 dtex fiber diameter from FiberVisions.

Binders in liquid form, such as latex emulsions, can comprise between about 0% and about 10% of the foam (by weight). In certain embodiments the non-fibrous binder can comprise between about 0.1% and 10% of the foam (by weight) or even between about 0.2% and about 5% or even between about 0.5% and about 2% of the foam (by weight). Binder fibers, when used, may be added proportionally to the other components to achieve the desired fiber ratios and structure while maintaining the total solids content of the foam below the amounts stated above. As an example, in some embodiments, binder fibers can comprise between about 0% and about 50% of the total fiber weight, and more preferably, between about 5% to about 40% of the total fiber weight in some embodiments.

Foam Stabilizers

The foam may optionally also include one or more foam stabilizers known in the art and that are compatible with the components of the foam and further do not interfere with the hydrogen bonding as between the cellulosic fibers. Foam stabilizing agents believed suitable for use in the present disclosure, without limitation, one or more zwitterionic compounds, amine oxides, alkylated polyalkylene oxides, or mixture or combinations thereof. Specific examples of foam stabilizers includes, without limitation, cocoamine oxide, isononyldimethylamine oxide, n-dodecyldimethylamine oxide, and so forth.

In some embodiments, if utilized, the foam stabilizer can comprise between about 0.01% and about 2% of the foam (by weight). In certain embodiments, the foam stabilizer can comprise between about 0.05% and 1% of the foam or even between about 0.1 and about 0.5% of the foam (by weight).

Additional Additives

In the methods as described herein, the foam forming process can include adding one or more additional additives. For example, one additional additive that can be added during the formation of the substrates 10 as described herein can be a superabsorbent materials (SAM). SAM is commonly provided in a particulate form and, in certain aspects, can comprise polymers of unsaturated carboxylic acids or derivatives thereof. These polymers are often rendered water insoluble, but water swellable, by crosslinking the polymer with a di- or polyfunctional internal crosslinking agent. These internally cross-linked polymers are at least partially neutralized and commonly contain pendant anionic carboxyl groups on the polymer backbone that enable the polymer to absorb aqueous fluids, such as body fluids. Typically, the SAM particles are subjected to a post-treatment to crosslink the pendant anionic carboxyl groups on the surface of the particle. SAMs are manufactured by known polymerization techniques, desirably by polymerization in aqueous solution by gel polymerization. The products of this polymerization process are aqueous polymer gels, i.e., SAM hydrogels that are reduced in size to small particles by mechanical forces, then dried using drying procedures and apparatus known in the art. The drying process is followed by pulverization of the resulting SAM particles to the desired particle size. Examples of superabsorbent materials include, but are not limited to, those described in U.S. Pat. No. 7,396,584 Azad et al., U.S. Pat. No. 7,935,860 Dodge et al., US2005/5245393 to Azad et al., US2014/09606 to Bergam et al., WO2008/027488 to Chang et al. and so forth. In addition, in order to aid processing, the SAM may be treated in order to render the material temporarily non-absorbing during the formation of the foam and formation of the highly-expanded foam. For example, in one aspect, the SAM may be treated with a water-soluble protective coating having a rate of dissolution selected such that the SAM is not substantially exposed to the aqueous carrier until the highly-expanded foam has been formed and drying operations initiated. Alternatively, in order to prevent or limit premature expansion during processing, the SAM may be introduced into the process at low temperatures.

In some embodiments incorporating SAM, the SAM can comprise between about 0% and about 40% of the foam (by weight). In certain embodiments, SAM can comprise between about 1% and about 30% of the foam (by weight) or even between about 10% and about 30% of the foam (by weight).

Other additional agents can include one or more wet strength additives that can be added to the foam in order to help improve the relative strength of the ultra-low density composite cellulosic material. Such strength additives suitable for use with paper making fibers and the manufacture of paper tissue are known in the art. Temporary wet strength additives may be cationic, nonionic or anionic. Examples of such temporary wet strength additives include PAREZ™ 631 NC and PAREZ® 725 temporary wet strength resins that are cationic glyoxylated polyacrylamides available from Cytec Industries, located at West Paterson, N.J. These and similar resins are described in U.S. Pat. No. 3,556,932 to Coscia et al. and U.S. Pat. No. 3,556,933 to Williams et al. Additional examples of temporary wet strength additives include dialdehyde starches and other aldehyde containing polymers such as those described in U.S. Pat. No. 6,224,714 to Schroeder et al.; U.S. Pat. No. 6,274,667 to Shannon et al.; U.S. Pat. No. 6,287,418 to Schroeder et al.; and US6365667 to Shannon et al., and so forth.

Permanent wet strength agents comprising cationic oligomeric or polymeric resins may also be used in the present disclosure. Polyamide-polyamine-epichlorohydrin type resins such as KYMENE 557H sold by Solenis are the most widely used permanent wet-strength agents and are suitable for use in the present disclosure. Such materials have been described in the following U.S. Pat. No. 3,700,623 to Keim; U.S. Pat. No. 3,772,076 to Keim; U.S. Pat. No. 3,855,158 to Petrovich et al.; US3899388 to Petrovich et al.; U.S. Pat. No. 4,129,528 to Petrovich et al.; U.S. Pat. No. 4,147,586 to Petrovich et al.; U.S. Pat. No. 4,222,921 to van Eenam and so forth. Other cationic resins include polyethylenimine resins and aminoplast resins obtained by reaction of formaldehyde with melamine or urea. Permanent and temporary wet strength resins may be used together in the manufacture of composite cellulosic products of the present disclosure. Further, dry strength resins may also optionally be applied to the composite cellulosic webs of the present disclosure. Such materials may include, but are not limited to, modified starches and other polysaccharides such as cationic, amphoteric, and anionic starches and guar and locust bean gums, modified polyacrylamides, carboxymethylcellulose, sugars, polyvinyl alcohol, chitosan, and the like.

If used, such wet and dry strength additives can comprise between about 0.01 and about 5% of the dry weight of cellulose fibers. In certain embodiments, the strength additives can comprise between about 0.05% and about 2% of the dry weight of cellulose fibers or even between about 0.1% and about 1% of the dry weight of cellulose fibers.

Still other additional components may be added to the foam so long as they do not significantly interfere with the formation of the highly-expanded stable foam, the hydrogen bonding as between the cellulosic fibers or other desired properties of the web. As examples, additional additives may include one or more pigments, opacifying agents, antimicrobial agents, pH modifiers, skin benefit agents, odor absorbing agents, fragrances, thermally expandable microspheres, pulverized foam particles and so forth as desired to impart or improve one or more physical or aesthetic attributes. In certain embodiments the composite cellulosic webs may include skin benefit agents such as, for example, antioxidants, astringents, conditioners, emollients, deodorants, external analgesics, film formers, humectants, hydrotropes, pH modifiers, surface modifiers, skin protectants, and so forth.

When employed, miscellaneous additives desirably comprise less than about 2% of the foam (by weight) and still more desirably less than about 1% of the foam (by weight) and even less than about 0.5% of the foam (by weight).

In some embodiments, the solids content, including the fibers or particulates contained herein, desirably comprise no more than about 40% of the foam. In certain embodiments the cellulosic fibers can comprise between about 0.1% and about 5% of the foam or between about 0.2 and about 4% of the foam or even between about 0.5% and about 2% of the foam.

Formation of Foam

The foaming fluid and any other surfactant(s) or other fibers or agents is acted upon to form a foam. In some embodiments, the foaming fluid and other components are acted upon so as to form a porous foam having an air content greater than about 50% by volume and desirably an air content greater than about 60% by volume. In certain aspects, the highly-expanded foam is formed having an air content of between about 60% and about 95% and in further aspects between about 65% and about 85%. In certain embodiments, the foam may be acted upon to introduce air bubbles such that the ratio of expansion (volume of air to other components in the expanded stable foam) is greater than 1:1 and in certain embodiments the ratio of air:other components can be between about 1.1:1 and about 20:1 or between about 1.2:1 and about 15:1 or between about 1.5:1 and about 10:1 or even between about 2:1 and about 5:1.

The foam can be generated by one or more means known in the art. Examples of suitable methods include, without limitation, aggressive mechanical agitation, injection of compressed air, and so forth. Mixing the components through the use of a high-shear, high-speed mixer is particularly well suited for use in the formation of the desired highly-porous foams. Various high-shear mixers are known in the art and believed suitable for use with the present disclosure. High-shear mixers typically employ a tank holding the foam precursor and/or one or more pipes through which the foam precursor is directed. The high-shear mixers may use a series of screens and/or rotors to work the precursor and cause aggressive mixing of the components and air. In a particular embodiment, a tank is provided having therein one or more rotors or impellors and associated stators. The rotors or impellors are rotated at high speeds in order to cause flow and shear. Air may, for example, be introduced into the tank at various positions or simply drawn in by the action of the mixer. While the specific mixer design may influence the speeds necessary to achieve the desired mixing and shear, in certain embodiments suitable rotor speeds may be greater than about 500 rpm and, for example, be between about 1000 rpm and about 6000 rpm or between about 2000 rpm and about 4000 rpm. In certain embodiments, with respect to rotor based high-shear mixers, the mixer maybe run with the foam until the disappearance of the vortex in the foam or a sufficient volume increase is achieved.

In addition, it is noted the foaming process can be accomplished in a single foam generation step or in sequential foam generation steps. For example, in one embodiment, all of the components may be mixed together to form a slurry from which a foam is formed. Alternatively, one or more of the individual components may be added to the foaming fluid, an initial mixture formed (e.g. a dispersion or foam), after which the remaining components may be added to the initially foamed slurry and then all of the components acted upon to form the final foam. In this regard, the water and foaming surfactant may be initially mixed and acted upon to form an initial foam prior to the addition of any solids. Fibers may then be added to the water/surfactant foam and then further acted upon to form the final foam. As a further alternative, the water and fibers, such as a high density cellulose pulp sheet, may be aggressively mixed at a higher consistency to form an initial dispersion after which the foaming surfactant, additional water and other components, such as synthetic fibers, are added to form a second mixture which is then mixed and acted upon to form the foam.

The foam density of the foam can vary depending upon the particular application and various factors, including the fiber stock used. In some implementations, for example, the foam density of the foam can be greater than about 100 g/L, such as greater than about 250 g/L, such as greater than about 300 g/L. The foam density is generally less than about 800 g/L, such as less than about 500 g/L, such as less than about 400 g/L, such as less than about 350 g/L. In some implementations, for example, a lower density foam is used having a foam density of generally less than about 350 g/L, such as less than about 340 g/L, such as less than about 330 g/L.

Foam Forming Zoned and/or Layered Substrate

A first supply 14 of fibers can be transported to a headbox 16, such as illustrated in FIG. 1, via conduit(s) 18. Although one conduit 18 is illustrated in FIG. 1 for transporting the first supply 14 of fibers to the headbox 16, it is contemplated that more than one conduit 18 can supply the first supply 14 of fibers to the headbox 16. A second supply 15 of fibers can also be transported to the headbox 16. In some embodiments, the second supply 15 of fibers can include different fibers than the first supply 14 of fibers. In some embodiments, the second supply 15 of fibers can include the same fibers as the first supply 14 of fibers. In some embodiments, the second supply 15 of fibers can be provided from a foam slurry that is different from the foam slurry providing the first supply 14 of fibers in at least one characteristic. The second supply 15 of fibers can be transported to the headbox 16 via conduit 19. It is contemplated that the second supply 15 of fibers can be transported to the headbox 16 in more than one conduit 19.

The headbox 16 illustrated in FIG. 1 can be a vertical twin-wire headbox 16, as generally known in the art. The headbox 16 as illustrated in FIG. 1 can include first and second foraminous elements 20, 22. The first and second foraminous elements 20, 22 can help define an interior volume 24 of the headbox 16. The headbox 16 can include an inlet 26 and an outlet 28. A series of vacuum elements 30 can be disposed adjacent each foraminous elements 20, 22. The vacuum elements 30 can help to dewater the foam that is delivered to the headbox 16 and deposited on the foraminous elements 20, 22.

The headbox 16 can include a machine direction 32, a cross-direction 34, and a z-direction 35 perpendicular to a plane defined by the machine direction 32 and the cross-direction 34 of the headbox 16. In FIG. 1, the machine direction 32 can be viewed in a downward direction, or be defined as extending from the inlet 26 of the headbox 16 to the outlet 28 of the headbox 16. Although the discussion herein is referred to with respect to a vertical twin-wire headbox 16, it is to be appreciated that the methods and apparatuses discussed herein can be utilized with other headbox 16 configurations and orientations.

Figure 2:
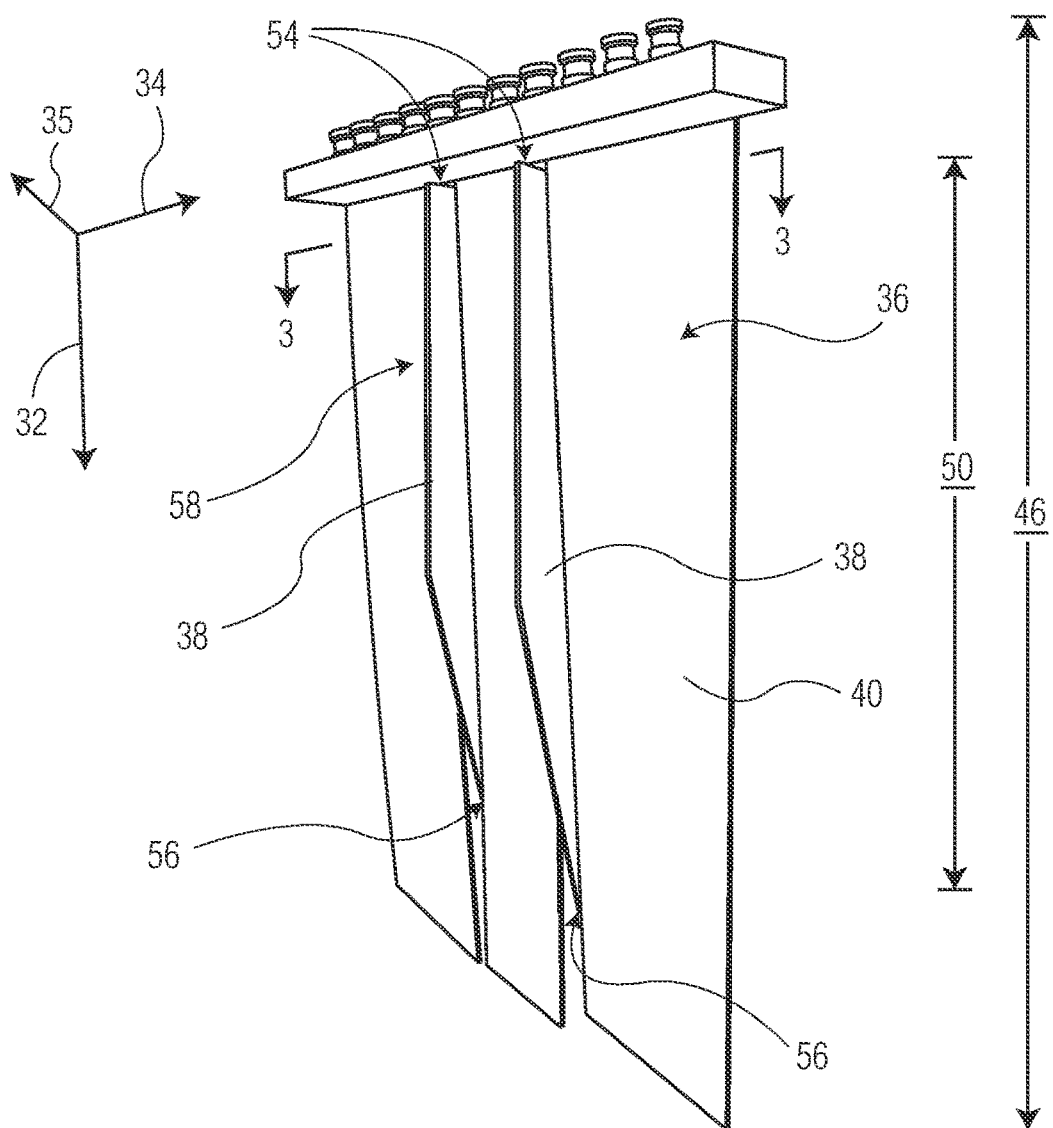
FIG. 2 is a top, perspective view of a divider, such as utilized in FIG. 1.
Figure 3:
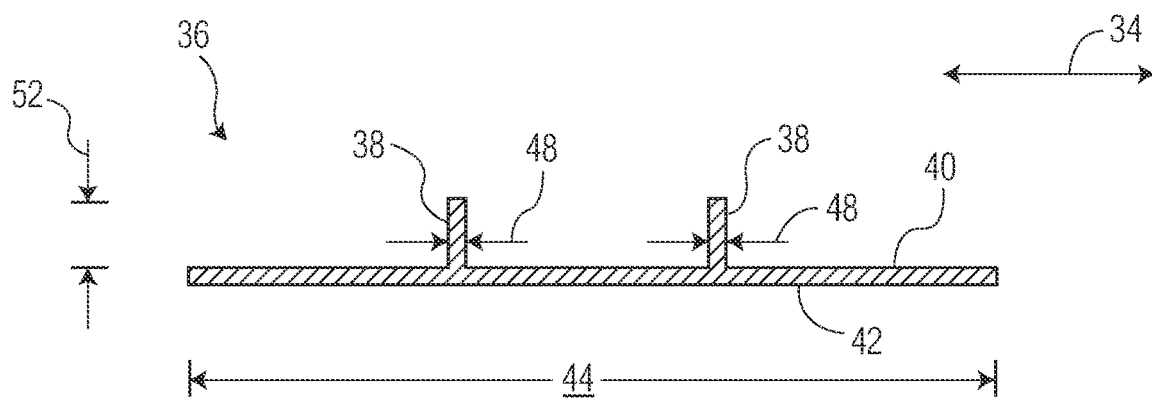
FIG. 3 is a cross-section view taken along line 3-3 from FIG. 2.
Figure 4:
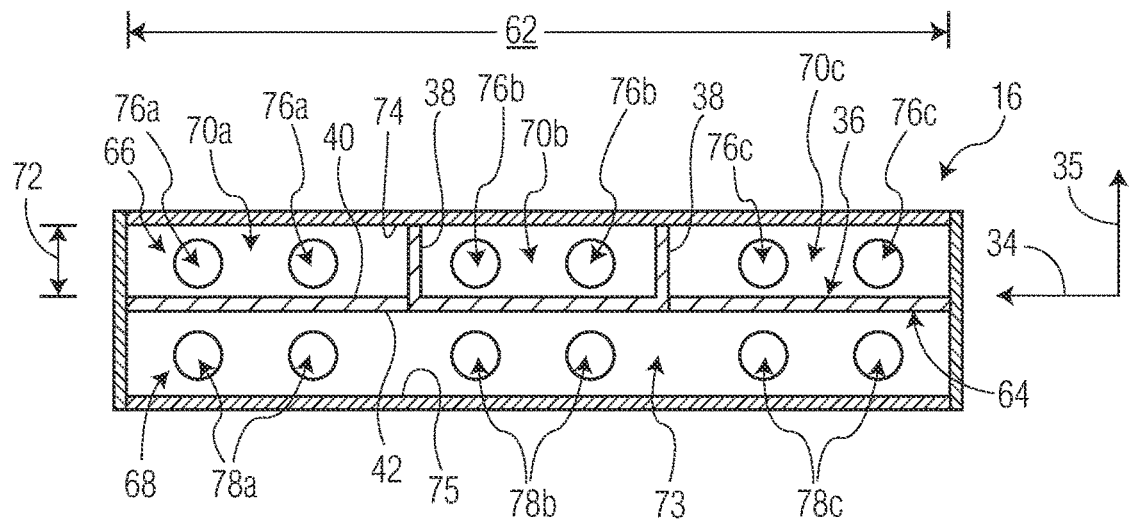
FIG. 4 is a top plan view of an exemplary inlet section to the headbox of FIG. 1

With reference to FIGS. 2-4, the headbox 16 can include a divider 36. The divider 36 can include at least one cross-directional divider 38. For example, in FIGS. 2-4, the divider 36 depicted includes two cross-directional dividers 38. One cross-directional divider 38 is spaced apart from the other cross-directional divider 38 in the cross-direction 34 of the headbox 16. In some embodiments, the divider 36 can include a first surface 40 and a second surface 42. The second surface 42 can be opposite from the first surface 40 of the divider 36. The divider 36 can include a width 44 in the cross-direction 34 and a length 46 in the machine direction 32. In some embodiments, the length 46 of the divider 36 can be configured to be at least 50% of the length L of the headbox 16 (as labeled in FIG. 1), or at least 60% of the length L of the headbox 16, or at least 65% of the length L of the headbox 16, or at least 70% of the length of the headbox, or at least 75% of the length L of the headbox 16.

Figure 6:
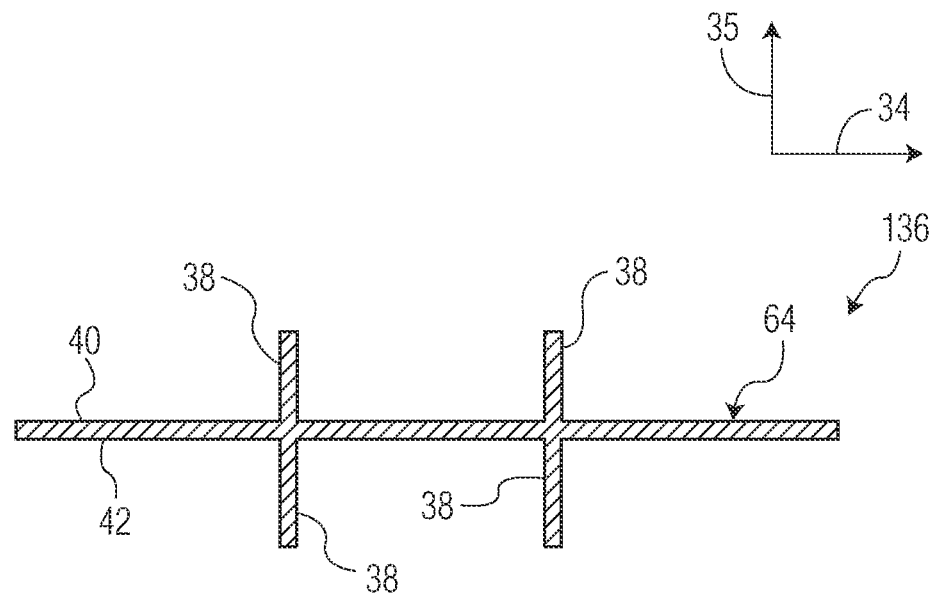
FIG. 6 is a cross-section view of an alternative divider that can be utilized in a headbox, such as illustrated in FIG. 1.

The cross-directional divider 38 can extend away from the first surface 40. In some embodiments, such as the embodiment depicted in FIGS. 2-4, the divider 36 can include two or more cross-directional dividers 38 that extend away from the first surface 40 in the same direction. However, it is contemplated that in some embodiments the divider 36 could include one or more cross-directional dividers 38 that extend away from the first surface 40 and one or more cross-directional dividers 38 that extend away from the second surface 42 of the divider 36, such as depicted in FIG. 6 and discussed further below. In some embodiments, the cross-directional divider 38 extends away from the first surface 40 in a direction substantially perpendicular to a plane defined by the first surface 40. In some embodiments, the cross-directional divider 38 can extend away from the second surface 42 in a direction substantially perpendicular to a plane defined by the second surface 42.

The cross-directional divider 38 can include a cross-directional thickness 48 and a machine-directional length 50. The cross-directional thickness 48 of the cross-directional divider 38 is to be measured in the cross direction 34 for the headbox 16. In some embodiments, the cross-directional thickness 48 of the cross-directional divider 38 can be between about 0.5 mm to about 10 mm. The machine-directional length 50 of the cross-directional divider 38 is to be measured in the machine direction 32 for the headbox 16 between a proximal end 54 of the cross-directional divider 38 and a distal end 56 of the cross-directional divider 38. In some embodiments, the machine-directional length 50 of the cross-directional divider 38 can vary based on the length 46 of the divider 36. In some embodiments, such as the embodiment depicted in FIG. 2, the machine directional length 50 of the cross-directional divider 38 can be less than the length 46 of the divider 36.

The height 52 of the cross-directional divider 38 is to be measured in a direction perpendicular to the machine direction 32 and the cross direction 34 of the headbox 16 and from the surface of the divider 36 from which it extends. As an example, the height 52 of the cross-directional divider 38 is measured from the first surface 40 of the divider 36 in a direction perpendicular to the machine direction 32 and the cross direction 34 of the headbox 16, such as illustrated in FIG. 3.

The height 52 of the cross-directional divider 38 can vary along the machine directional length 40 of the cross-directional divider 38. For example, in the embodiment depicted in FIG. 2, the height 52 of the cross-directional divider 38 at the proximal end 54 of the cross-directional divider 38 is greater than the height 52 of the cross-directional divider 38 at the distal end 56 of the cross-directional divider 38. In some embodiments, the cross-directional divider 38 can include a first section 58 that has a substantially constant height 52 and a second section 60 that has a decreasing height 52 along the machine-directional length 50 of the cross-directional divider 38. As illustrated in the embodiment of FIG. 2, the second section 60 of the cross-directional divider 38 can decrease in height 52 in a linear fashion. Of course, it is contemplated that the height 52 of the cross-directional divider 38 may decrease between a proximal end 54 and a distal end 56 of the cross-directional divider 38 in other ways. Not to be bound by theory, but it is believed that decreasing the height 52 along the machine-directional length 50 of the cross-directional divider 38 can help with intermingling of fibers between various zones in the headbox 16 if such a decrease in height creates a gap between the cross-directional divider 38 and the foraminous element 22, as will be discussed in more detail below.

FIG. 4 illustrates a cross-sectional view of divider 36 within the headbox 16, as viewed at the inlet 26 of the headbox 16. As depicted in FIG. 4, divider 36 can have a width 44 (as labeled in FIG. 3) that substantially spans across the width 62 of the internal volume 24 of the headbox 16 at the inlet section 26. In some embodiments, the width 44 of the divider 36 can be at least 90%, or more preferably at least 95%, of the width 62 of the internal volume 24 of the headbox 16 at the inlet section 26. The first surface 40 and the second surface 42 of the divider 36 can form a z-directional divider 64 for the headbox 16. In other words, the divider 36 can form a z-directional divider 64 by forming a first z-directional layer 66 and a second z-directional layer 68 within the headbox 16.

In some embodiments, the divider 36 can be positioned in the headbox 16 such that the z-directional divider 64 is evenly positioned between the internal surface 74 of the top of the headbox 16 and the internal surface 75 of the bottom of the headbox 16. Such a configuration provides for an equal thickness for the first z-directional layer 66 of the headbox 16 and the second z-directional layer 68 of the headbox 16. Of course, the divider 36 can be moved in a z-directional manner with respect to the headbox 16 to provide different target thicknesses for the first z-directional layer 66 of the headbox 16 and the second z-directional layer 68 of the headbox 16, and in turn, different thicknesses for the corresponding layers 82, 84 of a substrate as described later herein.

As also depicted in FIG. 4, the cross-directional dividers 38 can create zones 70a, 70b, 70c within the headbox 16, or within a particular z-directional layer in the headbox 16. In the embodiment depicted in FIG. 4, the two cross-directional dividers 38 can create a first zone 70a, a second zone 70b, and a third zone 70c that each form part of the first z-directional layer 66 of the headbox 16. For example, the first zone 70a and the second zone 70b are separated from one another by the left-most cross-directional divider 38 and the second zone 70b and the third zone 70c are separated from one another by the right-most cross-directional divider 38. When creating zones that are distinguished from one another in the headbox 16 in a cross-directional manner at the inlet 26 of the headbox 16, it is preferable that the cross-directional divider(s) 38 preferably have a height 52 (such as labeled in FIG. 3) that substantially spans the distance between the two surfaces that provide a thickness for a particular layer of the headbox 16 at least near the inlet 26 of the headbox 16 (e.g., at the proximal end 54 of the cross-directional divider 38). For example, in the embodiment depicted in FIG. 4, it is preferable if the cross-directional dividers 38 of the divider 36 include a height 52 (as labeled in FIG. 3) that substantially spans the distance 72 between the first surface 40 of the divider 36 and the internal surface 74 of the headbox 16 that defines the thickness of the first layer 66 in the headbox 16 at the inlet 26 of the headbox 16. For example, the height 52 of the cross-directional dividers 38 can be at least 90%, or more preferably at least 95%, of the distance 72 between the first surface 40 of the divider 36 and the internal surface 74 of the headbox 16 defining the thickness of the first layer 66 of the headbox 16.

While FIG. 4 illustrates an embodiment including a divider 36 with two cross-directional dividers 38 that extend from the first surface 40, it is contemplated that other arrangements for creating cross-directional zones within a headbox 16 can be created and utilized to create zoned substrates. For example, in some embodiments, a headbox 16 can include one or more cross-directional dividers 38, without any z-directional divider 64, such that there is only one z-directional layer 66 within the headbox 16. It is also contemplated that a divider 36 could have a single cross-directional divider 38 extending from only one surface 40 or 42 to create only two zones within a particular z-directional layer within the headbox 16, or there could be three or more cross-directional dividers 38 that create four or more zones within a particular z-directional layer within the headbox 16. As illustrated in FIG. 4, in some embodiments, the divider 36 can create a z-directional layer 68 that only includes a single zone 73. As will be described in other embodiments, the divider 36 can include at least one cross-directional divider 38 extending from the first surface 40 and at least one cross-directional divider 38 extending from the second surface 42 that create more than one zone in each of the z-directional layers 66, 68 of the headbox 16.

In embodiments that include a cross-directional divider 38 and a z-directional divider 64, the cross-directional divider(s) 38 can be integrally formed with the z-directional divider(s) 64. It is also contemplated that the cross-directional divider 38 can be formed separately from the z-directional divider 64, but be coupled to the z-directional divider 64, such as, for example, welds, adhesives, or other suitable bonding techniques.

The cross-directional divider(s) 38 and the z-directional divider(s) 64 can be formed from any suitable material. For example, the cross-directional divider(s) 38 and the z-directional divider(s) 64 can be formed from metals (e.g., steel, aluminum, etc.), plastics, or other suitable substances. In a preferred embodiment, the cross-directional divider(s) 38 and the z-directional divider(s) 64 can be formed from or coated with polytetrafluoroethylene (PTFE), as such dividers 38, 64 can prevent sticking of fibers, and particularly of some additives, such as superabsorbent material, to the dividers 38, 64.

Figure 5A:
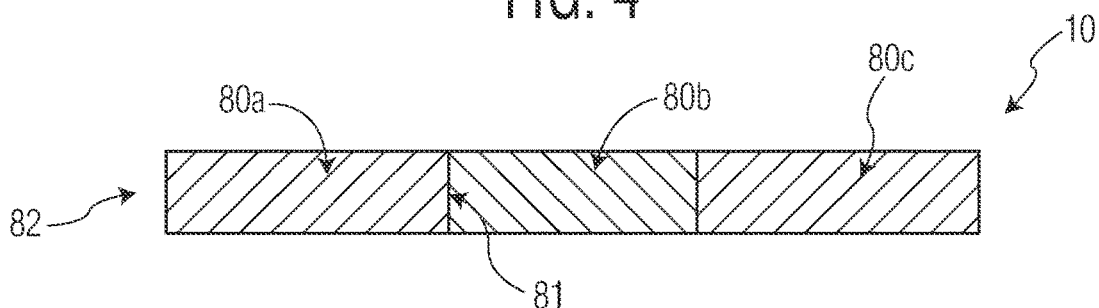
FIG. 5A is a cross-section view of an exemplary zoned substrate of the present disclosure that can be provided by the headbox and divider as illustrated in FIG. 4.

Supply of fibers and additional additives can be supplied to the various layers and zones of the headbox 16 to provide various configurations of a substrate. FIG. 4 also illustrates how fibers and/or additives can be provided to the headbox 16 to provide a zoned substrate 10, such as illustrated in FIG. 5A. For example, with the use a cross-directional divider 38 in headbox 16 as illustrated in FIG. 4, a first supply 14 of fibers can be transferred to the second zone 70b of the first layer 66 of the headbox 16, such as through conduit(s) 18 coupled to inlet ports 76b that supply the second zone 70b of the first layer 66 of the headbox 16. A second supply 15 of fibers can be transferred to the first zone 70a of the first layer 66 of the headbox 16, for example, such as through the conduit(s) 19 coupled to inlet ports 76a in the first zone 70a of the first layer 66 of the headbox 16. As illustrated in FIG. 1, the conduit 19 that provides the second supply 15 of fibers could be split to supply the first zone 70a and the third zone 70c, or there could be two separate conduits 19 that are connected to the second supply 15 of fibers and that supply the first and third zones 70a, 70c. In some embodiments of manufacturing a zoned substrate 10, such as the substrate 10 in FIG. 5A, the second supply 15 of fibers can also be transferred to the third zone 70c of the first layer 66 of the headbox 16, such as through inlet ports 76c that supply the third zone 70c of the first layer 66 of the headbox. Importantly, while pairs of inlet ports 76a, 76b, 76c are each shown as supplying the first zone 70a, the second zone 70b, and the third zone 70c of the first layer 66 of the headbox 16, respectively, it is contemplated that there could be a single inlet port or three or more inlet ports that supply a respective cross-directional zone and/or layer of the headbox 16.

The first supply 14 of fibers and the second supply 15 of fibers can be transferred through the headbox 16 in the machine direction 32 for the headbox 16 to provide the substrate 10. For example, referring back to FIG. 1, in a foam forming manufacturing technique the first supply 14 of fibers and the second supply 15 of fibers can be transferred to the headbox 16 in a foam slurry. As the first supply 14 of fibers and the second supply 15 of fibers are transferred through the headbox 16, the foam slurry incorporating the first supply 14 of fibers and the foam slurry incorporating the second supply 15 of fibers can be dewatered by vacuum elements 30 as the fibers are deposited on one or more of the foraminous elements 20, 22, as discussed above.

With the configuration noted above, the first supply 14 of fibers that is transferred to the second zone 70b of the headbox 16 and that is transferred through the headbox 16 can provide the substrate 10 as illustrated in FIG. 5A with a zone 80b. The second supply 15 of fibers that is transferred to the first zone 70a and the third zone 70c of the headbox 16 and that is transferred through the headbox 16 can provide the substrate 10 with zones 80a and 80c, respectively. The substrate 10 can be at least partially dewatered through the headbox 16 as it exits the headbox 16 at the outlet 28 of the headbox 16. The substrate 10 can be further dried, if necessary, and handled via equipment and processes as is known in the art.

Thus, FIG. 5A provides for a zoned substrate 10 including two or more zones within a particular layer of the substrate 10. Specifically, the zoned substrate 10 includes three zones 80a, 80b, 80c within a single layer 82 that forms zoned substrate 10. The zoned substrate 10 can provide the advantage of having a central zone 80b that includes fibers (with or without additives) that are different than the fibers (with or without additives) in zones 80a and 80c. As an example, the zoned substrate 10 could be configured to provide an absorbent material that has absorbent fibers in the first zone 80a, the second zone 80b, and the third zone 80c, but with an additive being present in the second zone 80b, such as superabsorbent material, but not in the first and third zones 80a, 80c. In another embodiment, the zoned substrate 10 could be configured to provide a combination of an intake/distribution material that has fibers in the first zone 80a and the third zone 80c that function particularly well as distribution fibers (e.g., such as a softwood pulp fiber, *eucalyptus* pulp fiber, or fine regenerated cellulose fiber and a binder fiber), and can have fibers in the second zone 80b that function particularly well as intake/acquisition fibers (e.g., such as a crimped PET fiber with a fiber diameter greater than 3 deniers and a binder fiber).

Figure 5B:
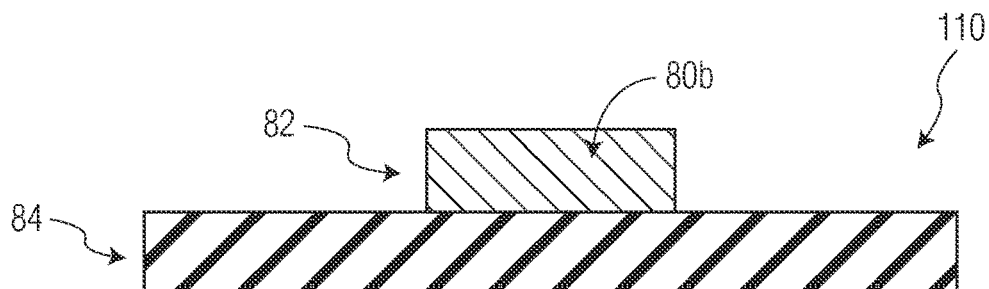
FIG. 5B is a cross-section view of an alternative exemplary zoned substrate of the present disclosure that can be provided by the headbox and divider as illustrated in FIG. 4.

In another example, a two layer zoned substrate 110 is illustrated in FIG. 5B. The zoned substrate 110 can include a first layer 82 and a second layer 84. Referring back to FIG. 4, a first supply 14 of fibers can be transferred to the second zone 70b of the first layer 66 of the headbox 16, such as through conduit(s) 18 coupled to inlet ports 76b that supply the second zone 70b of the first layer 66 of the headbox 16. A third supply 17 of fibers (as labeled in FIG. 1) can be supplied to the second layer 68 of the headbox 16, such as through conduit 21 coupled to inlet ports 78a, 78b, 78c. As previously noted, conduit 21 can be branched to feed multiple inlet ports 78a, 78b, 78c, and/or multiple conduits 21 can transfer the third supply 17 of fibers to inlet ports 78a, 78b, 78c of the second layer 68 of the headbox 16. In doing so, the first supply 14 of fibers can provide a first layer 82 of the substrate 110 in a central zone 80b and the third supply 17 of fibers can provide a second layer 84 of the substrate 110. Through the use of the two cross-directional dividers 38 in the headbox 16, the first layer 82 of the substrate 110 including fibers from the first supply 15 of fibers can be controlled to be of a narrower cross-directional width than the second layer 84 of the substrate 110 that includes fibers from the third supply 17 of fibers.

In some embodiments, the zoned substrate 110 can include a two layered substrate 110 in which the first layer 82 includes fibers that are different from the fibers of the second layer 84. For example, in one example, the zoned substrate 110 can be configured to provide an absorbent material that includes synthetic fibers in the first layer 82 in the zone 80b that function particularly well as intake/acquisition fibers (e.g., such as a crimped PET fiber with a fiber diameter greater than 3 deniers and a binder fiber) and absorbent fibers in the second layer 84, such as cellulosic fibers. In some embodiments, the second layer 84 can include fibers other than just cellulosic fibers, including other absorbent fibers and/or non-absorbent fibers. In some embodiments, the second layer can include an additive, such as a particulate of superabsorbent material.

Figure 5C:
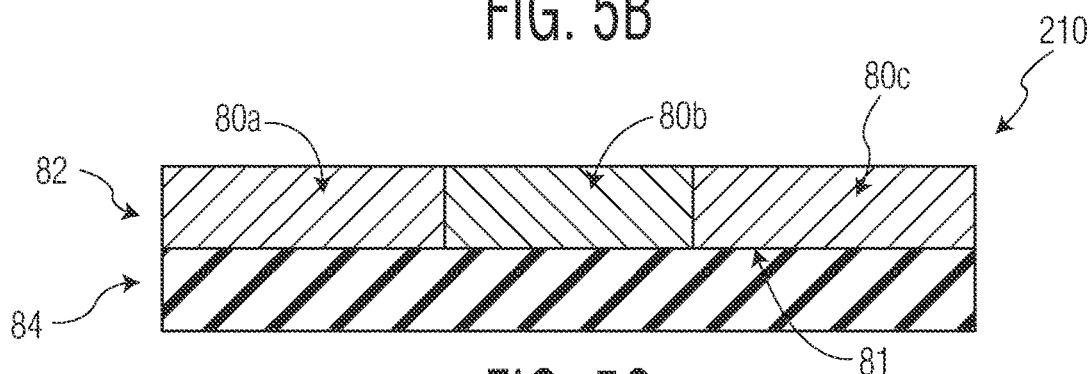
FIG. 5C is a cross-section view of yet another alternative exemplary zoned substrate of the present disclosure that can be provided by the headbox and divider as illustrated in FIG. 4.

Another embodiment of a two layer zoned substrate 210 is illustrated in FIG. 5C. The substrate 210 can include a first layer 82 and a second layer 84. The first layer 82 of the substrate 210 can be formed in some embodiments in a similar manner to substrate 10 as described above and as illustrated in FIG. 5A. Referring back to FIG. 4, a first supply 14 of fibers can be transferred to the second zone 70b of the first layer 66 of the headbox 16, such as through conduit(s) 18 (as labeled in FIG. 1) coupled to inlet ports 76b that supply the second zone 70b of the first layer 66 of the headbox 16. A second supply 15 of fibers (as labeled in FIG. 1) can be transferred to the first zone 70a and the third zone 70c of the headbox 16 and can be transferred through the headbox 16 to provide the first layer 82 of the substrate 210 with zones 80a and 80c, respectively. A third supply 17 of fibers (as labeled in FIG. 1) can be supplied to the second layer 68 of the headbox 16, such as through conduit 21 coupled to inlet ports 78a, 78b, 78c. In such an embodiment, the first supply 14 of fibers can provide a first layer 82 of the substrate 210 with a second zone 80b and the second supply 15 of fibers can provide the first layer 82 of the substrate 210 with the first and second zones 80a, 80c, respectively, that surround the second zone 80b in the first layer 82. The third supply 17 of fibers can provide a second layer 84 of the substrate 210. The cross-directional location of the two cross-directional dividers 38 in the headbox 16 can control the cross-directional width of each zone 80a, 80b, 80c in the first layer 82 of the substrate 210.

In some embodiments, the zoned substrate 210 of FIG. 5C can include a two layered substrate 210 in which the first layer 82 includes fibers that are different from the fibers of the second layer 84. The zoned substrate 210 can provide the advantage of having a central zone 80b that includes fibers (with or without additives) that are different than the fibers (with or without additives) in zones 80a and 80c within the first layer 82 of the substrate 210. As an example, the zoned substrate 210 could be configured to provide an absorbent material that has fibers in the first zone 80a and the third zone 80c that function particularly well as distribution fibers (e.g., such as a softwood pulp fiber, *eucalyptus* pulp fiber, or crosslinked pulp fiber and a binder fiber), and can have fibers in the second zone 80*b* that function particularly well as intake/acquisition fibers (e.g., such as a crimped PET fiber with a fiber diameter greater than 3 deniers and a binder fiber). The substrate 210 can also include binder material, such as binder fibers, in one or more zones 80*a*, 80*b*, 80*c* of the first layer 82. In some embodiments, the substrate 210 can include absorbent fibers in the second layer 84 that function well as absorbent fibers, and in some preferred embodiments, can include additional fibers and/or additives in the second layer 84. For example, the second layer 84 can be configured to include binder fibers and/or particulates such as superabsorbent material.

Of course, a variety of other configurations of zoned substrates can be configured based on the divider 36 including two cross-directional dividers 38 and a single z-directional divider 64 as shown and described above based on the fiber and additive configurations to various zones and layers of the headbox 16.

Additionally, other zoned and/or layered substrates can be made through the construction of different dividers for the headbox 16. As but one additional example, another alternative divider 136 is illustrated in FIG. 6. The divider 136 can include a first surface 40 that includes two cross-directional dividers 38 spaced apart from one another that extend away from the first surface 40. The divider 136 can include a second surface 42 that includes two cross-directional dividers 38 spaced apart from one another that extend away from the second surface 42. As illustrated in FIG. 6, the cross-directional dividers 38 extending away from the first surface 40 can be cross-directionally aligned with the cross-directional dividers 38 extending away from the second surface 42. However, it is contemplated that the spacing of the cross-directional dividers 38 on the first and second surface 40, 42 in the cross-direction 34 of the headbox 16 can be varied based on the resultant zoned substrate that is desired to be manufactured. Additionally, it is contemplated that the divider 136 could include only one cross-directional divider 38 on one or more of surfaces 40, 42 and/or three or more cross-directional dividers 38 on one or more of surfaces 40, 42.

Figure 7:
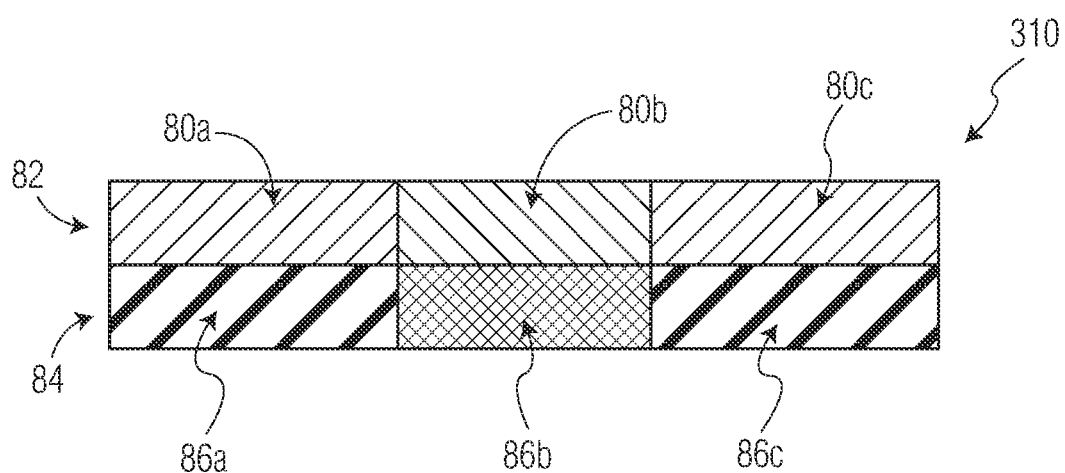
FIG. 7 is a cross-section view of another zoned substrate of the present disclosure that can be provided by the headbox and divider as illustrated in FIGS. 1 and 6.

FIG. 7 illustrates an exemplary zoned substrate 310 that can be manufactured by utilizing divider 136 in headbox 16 as described in the processes noted above with respect to FIGS. 1 and 4. For example, the zoned substrate 310 can include a first layer 82 and a second layer 84. The first layer 82 can include zones 80*a*, 80*b*, and 80*c*. The second layer 84 can include zones 86*a*, 86*b*, 86*c*.

As discussed above with respect to other embodiments of zoned substrates 10, 110, 210, one or more of the zones 80*a*, 80*b*, 80*c* in the first layer 82 and one or more of the zones 86*a*, 86*b*, 86*c* can by supplied by various supplies of fibers (with or without additives) that can provide various characteristics to the zoned substrate 310. As but one example, the first layer 82 of the zoned substrate 310 can be configured such that the second zone 80*b* includes fibers from a first supply 14 of fibers and a first zone 80*a* and third zone 80*c* include fibers from a second supply 15 of fibers. As discussed above, one preferable construction for such a layer 82 for a zoned substrate 310 may be to have the fibers from the first supply 14 of fibers in the second zone 80*b* include fibers that provide particular benefits for intake/acquisition functionality (e.g. a crimped PET fiber with a fiber diameter greater than 3 deniers and a binder fiber fibers). The fibers from the second supply 15 of fibers in the first and third zones 80*a*, 80*c*, respectively, of the first layer 82 can include fibers that provide particular benefits for distribution functionality (e.g., a softwood pulp fiber, *eucalyptus* pulp fiber, or crosslinked pulp fiber and a binder fiber fibers).

The second layer 84 can include first and third zones 86*a*, 86*c*, respectively, that include fibers from a third supply 17 of fibers that may include absorbent fibers. The second zone 86*b* of the second layer 84 of the substrate 310 can include particulates, such as from a supply 23 of particulates (e.g., SAM), as labeled in FIG. 1. The supply 23 of particulates can be transferred to the headbox 16 via a conduit 25. The supply 23 of particulates, in some embodiments, can also include fibers, such as, but not limited to, absorbent fibers. As a result, the second layer 84 of the substrate 310 can include first and third zones 86*a*, 86*c*, respectively, that can include absorbent fibers and can include a second zone 86*b* that includes additional additives (such as SAM) and/or absorbent fibers.

As can be seen from the examples of the substrates 10, 110, 210, 310 as described herein, the use of one or more cross-directional dividers 38, and where desired, one or more z-directional dividers 64, can provide a very functionalized, zoned substrate 10, 110, 210, 310 with various zones being created for enhancements of specific functionality for the end use in which the substrate 310 may be used in. In some embodiments, the zoned substrates as described herein can be utilized as part of or as an absorbent system in a personal care absorbent article. For example, the substrates 10, 110, 210, 310 can be utilized as part of an absorbent system in an absorbent article. It is also contemplated that the substrates 10, 110, 210, 310 could be utilized as part of or an entire absorbent article itself other than a personal care absorbent article, such as, for example a wipe, wiper, bath or facial tissue, or towel.

Not to be bound by theory, but it is believed that the use of z-directional dividers 64 and/or cross-directional dividers 38 can provide enhanced control of purity gradients at the interface between layers of a substrate and at the interface between adjacent zones within a particular layer of the substrates, respectively. For example, it is believed that that the height 52 of the cross-directional dividers 38 with respect to the dimensions of the headbox 16 can help separate zones (e.g., 70*a*, 70*b*, 70*c*) within a layer (e.g., 66) of the headbox 16 to control the fibers that are being transferred through the headbox 16 and formed into a substrate having interfaces 81 between zones (e.g., 80*a*, 80*b*, 80*c*) of a substrate 10 with a higher purity gradient. In embodiments that have a gap between the cross-directional divider 38 and the headbox 16, fibers from adjacent zones (e.g., 70*a*, 70*b*, 70*c*) of the headbox 16 can intermingle in such a gap area as the fibers are transferred through the headbox 16, and thus, can create zones (e.g., 80*a*, 80*b*, 80*c*) of a substrate 10 with a lower purity gradient. A similar intermingling could occur between layers (e.g., 66, 68) in the headbox 16 by having a z-directional divider 64 that has a width 44 that does not span the full width of the headbox 16.

In addition, it is believed that the machine directional length 50 of the cross-directional dividers 38 may be particularly controlled to provide a desired purity gradient between adjacent zones within the substrate (e.g., zones 80*a*, 80*b* in substrate 10 based on zones 70*a*, 70*b* of headbox 16). For example, it is believed that by having a cross-directional divider 38 that is shorter in length, a lower purity gradient can be achieved between adjacent zones (e.g., 80*a*, 80*b*) of a substrate as compared to a longer cross-directional divider 38. By having a shorter machine directional length 50 of the cross-directional divider 38, more fiber intermixing can occur at the interface 81 (labeled in FIG. 5A) between adjacent zones (e.g., 80a, 80b) of the substrate 10 after the cross-directional divider 38 and create a lower purity gradient at interface 81. A longer machine directional length 50 of the cross-directional divider 38 can allow for greater formation of the substrate through the headbox 16 while the fibers are still relatively contained within separate zones, and thus, decrease the amount of fiber and/or particulate intermixing between adjacent zones (e.g., 80a, 80b) of a substrate while the substrate is being formed and transferring through the headbox 16, and thus, create a higher purity gradient at interface 81.

In a similar respect, the machine directional length 46 of the divider 36 (which can also be the machine directional length of the z-directional divider 64) can help control a purity gradient between adjacent layers within the substrate (e.g., layers 82, 84 in substrate 210 based on layers 66, 68 of headbox 16). For example, a divider 36 having a shorter machine directional length 46 can provide a lower purity gradient at an interface 81 between adjacent z-directional layers (e.g., 82, 84) of a substrate as compared to a longer machine directional length 46 of the divider 36. A longer machine directional length 46 of the divider (and thus, the machine directional length of the z-directional divider 64) can allow for greater formation of the substrate through the headbox 16 while the fibers are still relatively contained within separate layers, and thus, decrease the amount of fiber and/or particulate intermixing at the interface 81 between adjacent layers (e.g., 82, 84) while the substrate is being formed and transferring through the headbox 16, and thus, create a higher purity gradient at interface 81. In some embodiments, it is preferable to have a machine directional length 46 of the divider 36 that is at least 50%, or at least 55%, or at least 60%, or at least 65%, or at least 70%, or at least 75% or more of the machine directional length L of the headbox 16.

It is believed that there may be advantages to having some substrates formed with lower purity gradients at the interface 81 between adjacent layers and/or zones, whereas there may be advantages to having some substrates formed with higher purity gradients at the interface 81 between adjacent layers and/or zones.

EXAMPLES

Experimental codes were formed utilizing a foam-forming method as described above with respect to FIG. 1 along with varying the divider construction. Purity gradients were measured at various interfaces 81 between zones of the substrates to determine how well a divider 36 including at least one cross-directional divider 38 can control the mixing at an interface 81 between zones. Relative layer thicknesses were also measured to determine the ability to control a relative thickness of a particular layer with respect to a target relative thickness setting in the headbox 16.

The surfactant used in the foam slurry for each code was Stantex H 215 UP, available from Pulcra Chemicals, which is an aqueous solution of alkyl polyglucosides based on natural fatty alcohol C8-C10. The codes were produced to attempt to make a substrate similar to the substrate 210 shown in FIG. 5C that includes three cross-directional zones 80a, 80b, 80c in a first layer 82. The second layer 84 was desired to have a uniform construction, or in other words, only a single zone. To provide such a configuration, reference is made to the headbox 16 configuration of FIG. 4. The inlets 76a of the first zone 70a of the first layer 66 of the headbox 16 and inlets 76c of the third zone 70c of the first layer 66 of the headbox 16 were provided with exemplary distribution layer materials of crosslinked cellulosic CMC 535 fibers and T 255 binder fibers. The inlets 76b of the second zone 70b of the first layer 66 of the headbox 16 were provided with exemplary intake layer materials of synthetic based fibers of PET fibers and T 255 binder fibers. All of the inlets 78a, 78b, and 78c of the second layer 68 of the headbox 16 were provided with materials to construct an absorbent layer by providing NBSK fibers, crosslinked cellulosic CMC 535 fibers, T 255 binder fibers, and superabsorbent material particulates.

Table 1 provides three exemplary codes that were formed utilizing fiber and/or particulates in the layers 66, 68 of the headbox 16 as described above to provide substrates 210A, 210B, and 210C. The only variable between codes documented in Table 1 was the type of divider 36 (or lack thereof) used with the headbox 16 to produce each substrate. For code A, a divider 36 including two cross-directional dividers 38 extending from the first surface 40 of the divider 36 was used, such as the divider 36 illustrated in FIG. 3 to make substrate 210A. For code B, a divider 36 including no cross-directional dividers 38 was used, such that the divider 36 only provided a z-directional divider 64 to make substrate 210B. For code C, no divider 36 was used in the headbox 16 to make substrate 210C. In each of the codes, a small percentage of colored fiber was added to the center zone 80b for first layer 82 to help visually depict the amount of mixing between adjacent zones and layers of each material code. The colored fiber used in the center zone 80b was an acrylic fiber with 3 mm fiber length and was provided at 3 wt % in the center zone 80b of the first layer 82 based on total weight of the fibers at that zone, approximately 1.2 gsm.

TABLE 1

Material Code Information

| | Layer 1 | | | | Layer 2 | | | | | |
|---|---|---|---|---|---|---|---|---|---|---|
| | Outside zones | | Center Zone | | Absorbent body | | | | | |
| Code | CMC 535 fibers (gsm) | T255 binder fibers (gsm) | PET curly fibers (gsm) | T255 binder fibers (gsm) | T255 binder fibers (gsm) | NBSK fibers (gsm) | CMC 535 fibers (gsm) | SAM (gsm) | % binder | % SAM |
| A | 31 | 9 | 26 | 14 | 23 | 30 | 23 | 400 | 4.8 | 84 |
| B | 31 | 9 | 26 | 14 | 23 | 30 | 23 | 400 | 4.8 | 84 |
| C | 31 | 9 | 26 | 14 | 23 | 30 | 23 | 400 | 4.8 | 84 |

Figure 8A:
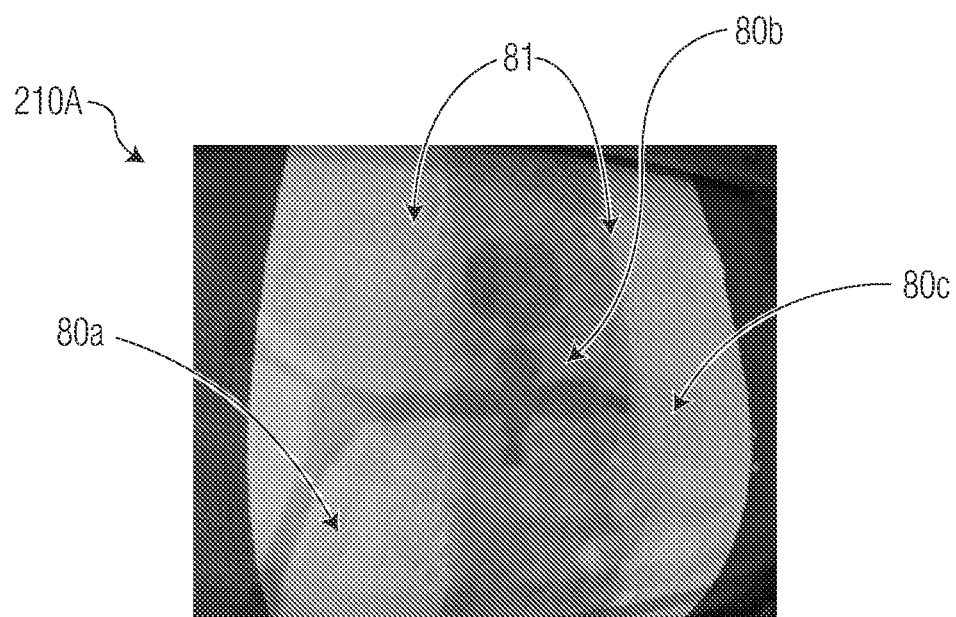
FIG. 8A is a photograph of an exemplary zoned substrate produced by a headbox and divider as illustrated in FIG. 4.
Figure 8B:
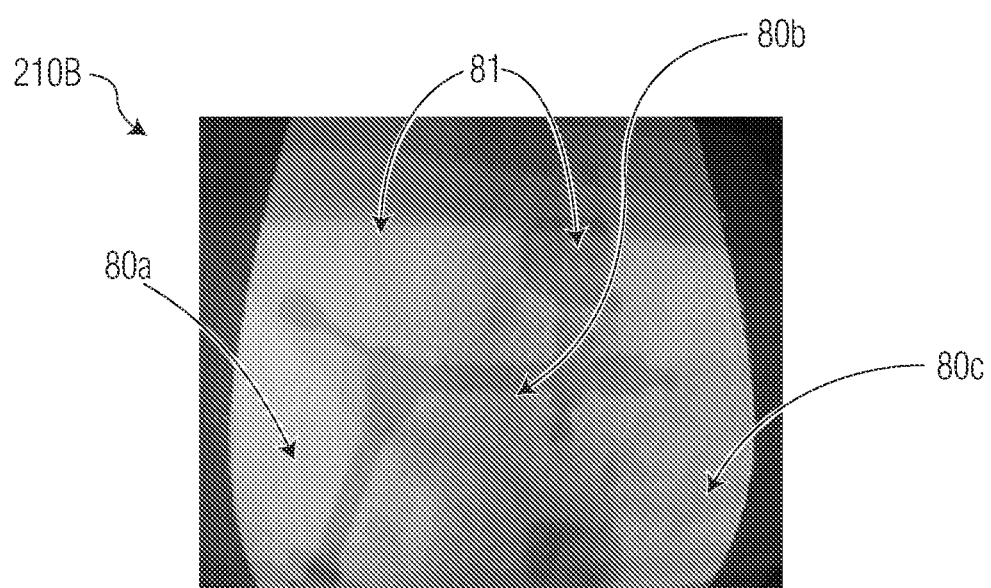
FIG. 8B is a photograph of an exemplary zoned substrate produced by a divider with no cross-directional dividers.
Figure 8C:
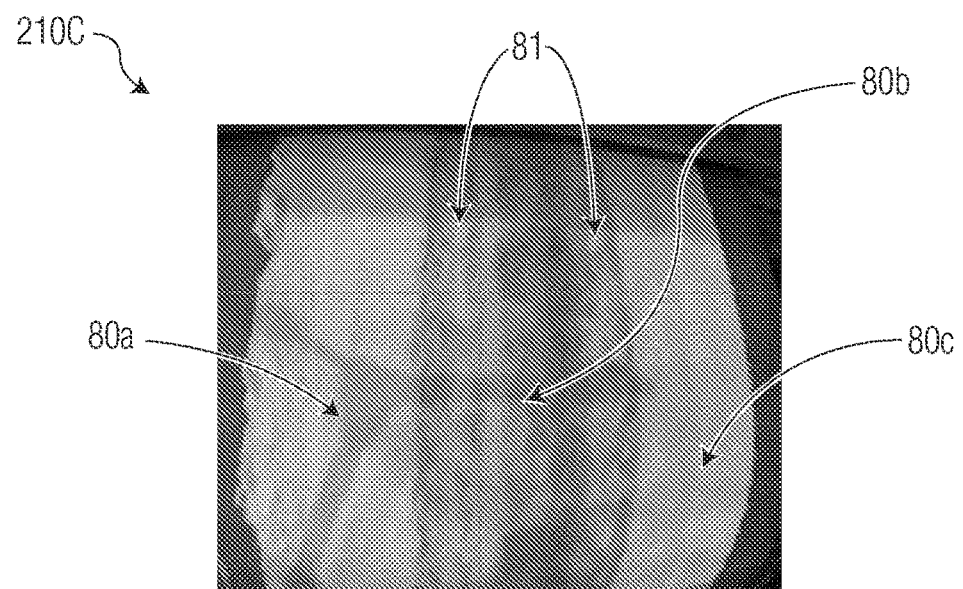
FIG. 8C is a photograph of a zoned substrate that was produced by a headbox with no divider.

FIGS. 8A-8C provide photographs depicting the substrates 210A, 210B, 210C formed by material Codes A, B, and C, respectively. The colored fibers that were used in the center zone 80b help visually demonstrate the amount of mixing occurring at an interface 81 between adjacent zones 80a and 80b and zones 80b and 80c in the substrates. For example, FIG. 8A that used a divider 36 including two cross-directional dividers 38 depicts the colored fibers of zone 80b (and thus the other fibers of the center zone 80b) of the substrate 210A were relatively contained between the interfaces 81 between itself and zone 80a and zone 80c. However, FIG. 8B that depicts a substrate 210B that used a divider 36 without any cross-directional dividers 38 and FIG. 8C that depicts a substrate 210C that did not use a divider 36 whatsoever shows a significantly higher amount of dispersion of the colored fiber from the center zone 80b at the interfaces 81 between zone 80a and 80b and between zone 80b and zone 80c. Thus, Codes B and C providing substrates 210B, 210C visually show a lower purity level of the interfaces 81 between zones 80a and 80b, and between 80b and 80c in the first layer 82.

Substrate samples from each experimental code substrates 210A, 210B, 210C were harvested for analysis according to the Purity Gradient Test Method and Layer Thickness Test Method as described in the Test Methods section herein. The Purity Gradient Test Method provides quantifiable characteristics for the amount of mixing at an interface between adjacent zones of a layer, as documented in Table 2.

TABLE 2

Results of Purity Gradient Testing for Adjacent Zones within a Layer

|  | Code A (Substrate 210A) | | Code B (Substrate 210B) | | Code C (Substrate 210C) | |
| --- | --- | --- | --- | --- | --- | --- |
|  | zone transition width (cm) | zone transition slope (gray/cm) | zone transition width (cm) | zone transition slope (gray/cm) | zone transition width (cm) | zone transition slope (gray/cm) |
| Average | 2.5 | 52 | 3.9 | 28 | 3.8 | 25 |
| Std. Dev. | 0.3 | 9 | 0.5 | 1 | 0.5 | 9 |
| Max. | 2.8 | 63 | 4.4 | 30 | 4.3 | 40 |
| Min. | 2.1 | 43 | 3.3 | 27 | 3.4 | 16 |
| n | 5 | 5 | 5 | 5 | 5 | 5 |

The results of the Purity Gradient testing for adjacent zones within a layer of a substrate from Table 2 show that a cross-directional divider 38 provides a substantial increase in control of the amount of mixing between adjacent zones within a layer of a substrate. For example, Code A demonstrated a substrate 210A having two zones in a layer with an interface having a purity gradient that includes a transition width of 2.5 cm, whereas Codes B and C only provided transition widths of 3.9 cm and 3.8 cm, respectively, for substrates 210B and 210C. Thus, preferable foam-formed substrates including adjacent zones in a layer can provide an interface between zones having a transition width of less than 3.8 cm, or more preferably, less than 3.0 cm., or more preferably, less than 2.8 cm.

Additionally, Code A demonstrated a substrate 210A having two zones in a layer with an interface having a purity gradient that includes a transition slope of 52 gray/cm, whereas Codes B and C only provided a substrate 210B and 210C with an interface having a purity gradient that includes a transition slope of 28 gray/cm and 25 gray/cm, respectively. The higher the transition slope of the purity gradient, the greater the level of purity exists at the interface between zones. Thus, preferable foam-formed substrates including adjacent zones in a layer can provide an interface between zones having a transition slope of greater than 28 gray/cm, or more preferably greater than 30 gray/cm, or even more preferably greater than 40 gray/cm.

Figure 10:
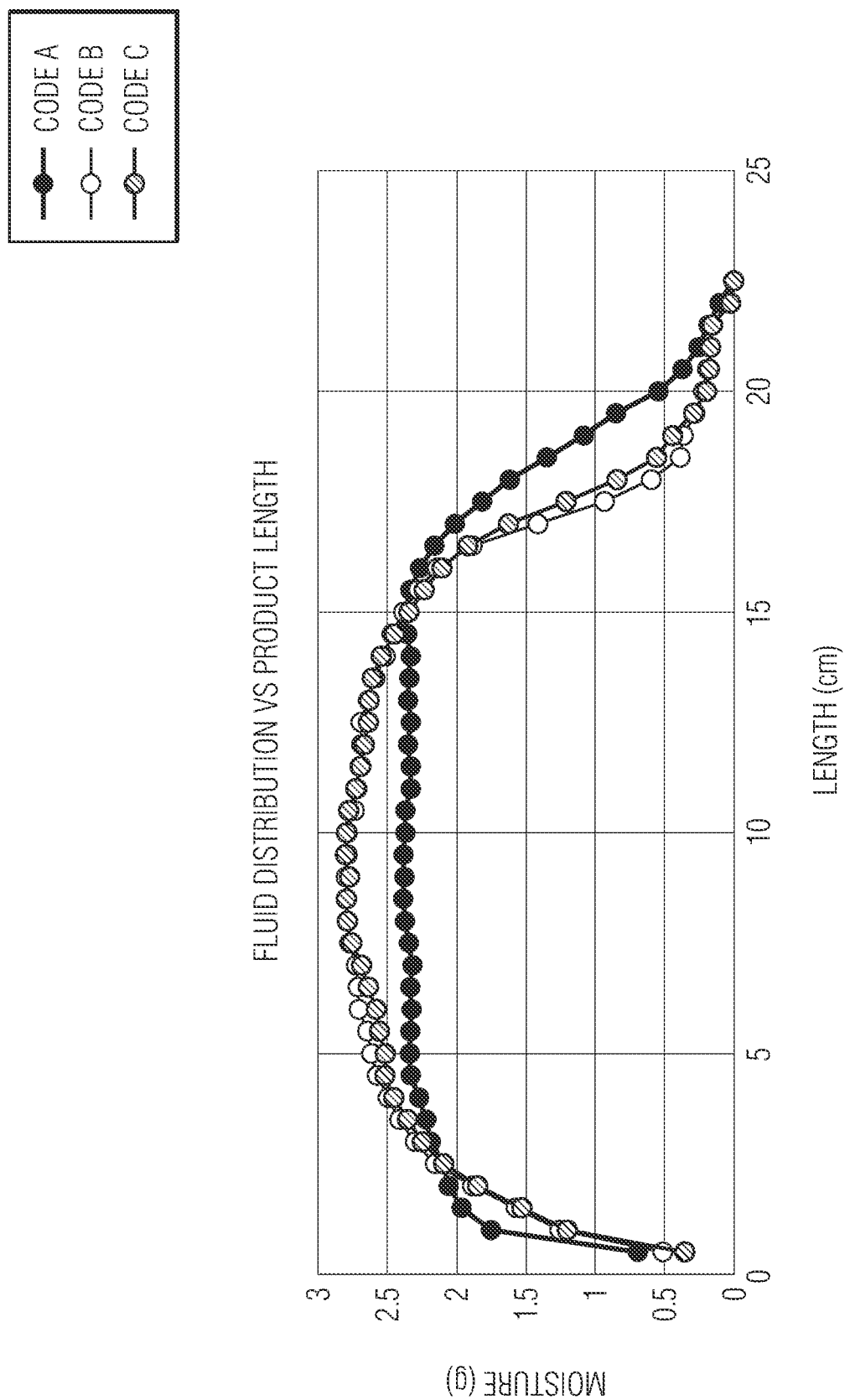
FIG. 10 is a graph depicting fluid distribution versus product length for exemplary codes.

By using a foam forming process with a divider 36 having cross-directional dividers 38, a substrate can be produced with an interface 81 between adjacent zones that provides a level of beneficial mixing to provide for proper integrity of the structure and fluid distribution between adjacent zones, yet the mixing can be controlled sufficiently at the interface 81 to still provide sufficient purity between different zones such that the intended purpose of different zones based on their fiber composition selection can be accomplished for the substrate 210. For example, FIG. 10 shows the efficiency of Code A in comparison to Codes B and C in terms of fluid distribution per product length. As shown in FIG. 10, Code A demonstrated a more even distribution of fluid for the entire substrate. Specifically, the moisture was lower near the insult as it was more evenly distributed throughout the length of the substrate. Code A demonstrated a higher moisture level than Code B or Code C at approximately 16-17 cm of length of the substrate. By having more efficient fluid distribution throughout the length of a substrate, substrates can be created that have lower amounts of material to perform the same functionality, and thus, provide raw material and cost savings for a particular intended end use. If used in personal care absorbent articles, the enhanced fluid distribution efficiency can also lead to thinner products, which may be more flexible, discrete, and/or comfortable for an end user.

Additionally, higher purity gradients between zones and/or layers can provide enhanced fluid intake rates due to distinctive intake and distribution zones in the first layer and an absorbent layer in the second layer. By having a higher purity gradient between zones and/or layers, absorbent substrates used in absorbent articles can perform multiple liquid handling functions, such as intake, distribution, and storage, such as for use in diapers or wiping, which can include fluid pick-up and lock-up, in multiple different structures that are designed for such particular functions. Notably, this is completed without the use of adhesives at such interfaces, as with other substrates in the prior art that look to make absorbent composites from separate materials that are adhered together. Adhesives at such interfaces can lead to lower performance of distribution and intake as the adhesives can act as a barrier to fluid handling.

Figure 9A:
FIG. 9A is a microCT image of a cross-section of the substrate of FIG. 8A.
Figure 9B:
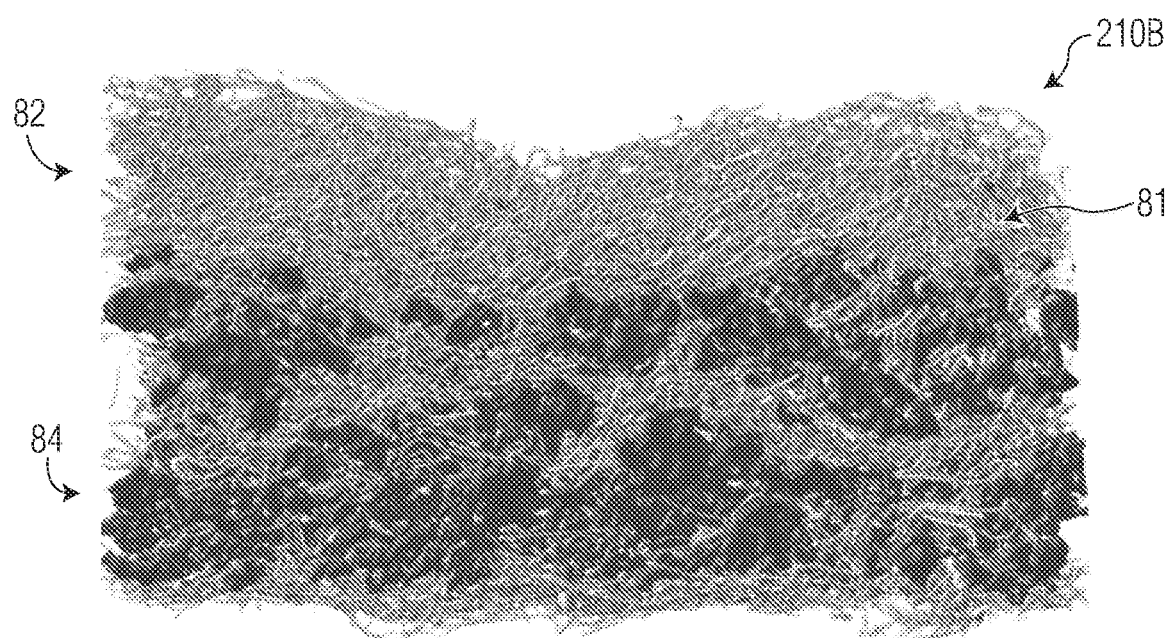
FIG. 9B is a microCT image of a cross-section of the substrate of FIG. 8B.
Figure 9C:
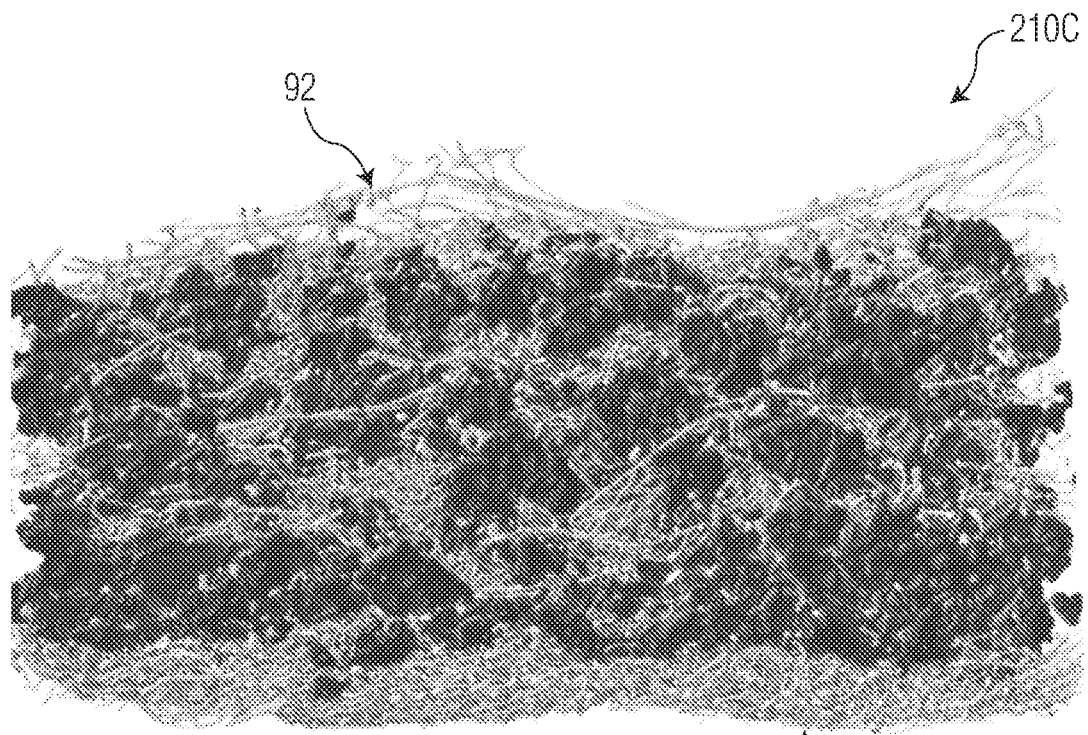
FIG. 9C is a microCT image of a cross-section of the substrate of FIG. 8C.

Layer relative thicknesses and purity of layers can also be controlled more readily through the use of dividers 36 that provide a z-directional divider 64. For the testing herein involving substrates 210A, 210B, 210C including superabsorbent material, the Layer Relative Thickness Test Method was utilized that employed microCT equipment. The Layer Relative Thickness Test Method is described in detail in the Test Methods section herein. Cross-sectional images of material Codes A-C providing substrates 210A-210C described above were taken utilizing microCT imaging equipment and are depicted in FIGS. 9A-9C, respectively. Table 3 provides the results of the relative layer thickness for a substrate 210 including a second layer 84 that includes superabsorbent material particles, where the relative thickness of the layer is measured as a percentage of the overall thickness of the substrate.

TABLE 3

Second Layer Relative Thickness Results

|  | Code A (Substrate 210A) Second Layer Relative Thickness | Code B (Substrate 210B) Second Layer Relative Thickness | Code C (Substrate 210C) Second Layer Relative Thickness |
| --- | --- | --- | --- |
| Average | 34% | 53% | 70% |
| Std. Dev. | 6% | 8% | 8% |
| n | 7 | 7 | 7 |

The relative layer thickness results documented in Table 3 demonstrate that the use of a divider 36 providing a z-directional divider 64 in the headbox 16 provides substantially more control over the purity of the layers 82, 84, and thus, more control over the layer relative thickness of a substrate 210, particularly where a layer includes particulate material (e.g., superabsorbent material particles). In producing Codes A and B (substrates 210A and 210B), the divider 36 was set up in the headbox 16 such that the divider 36 was evenly spaced in the z-directional 35 thickness of the headbox 16 (as illustrated in FIG. 4) to try to produce a second layer 84 of the substrate that had the same z-directional 35 thickness as the first layer 82. In other words, the divider 36 was positioned in the headbox 16 such that the z-directional divider 64 was evenly positioned between the internal surface 74 of the top of the headbox 16 and the internal surface 75 of the bottom of the headbox 16. The z-directional divider 64 was also configured to extend approximately 66% into the length of the headbox 16. On the other hand, Code C (substrate 210C) did not include any divider 36 in the headbox 16. With such a configuration of the divider 36 in the headbox 16 for producing Codes A and B, the divider 36 including a z-directional divider 64 provided for significantly more control of the superabsorbent material particles in the substrate for Codes A and B (substrates 210A and 210B) in comparison to Code C (substrate 210C), and thus, more control over the relative thickness of the second layer 84 including such particulates.

Specifically, as documented in Table 3, Code A and Code B providing substrates 210A and 210B utilizing a divider 36 to separate first layer 82 from second layer 84 provided a second layer 84 relative thickness of 34% and 53% of the total thickness of the substrate 210A, 210B, respectively, whereas Code C providing substrate 210C that was manufactured without utilizing a divider 36 provided a relative thickness of the second layer 84 that was 70% of the total thickness of the substrate 210C. Because the headbox 16 and divider 36 within the headbox 16 were configured to provide a target thickness in which the first layer 82 and a second layer 84 had equal thickness, Codes A and B displayed the ability to control the thickness of the second layer 84 including particulates (such as SAM particulates) to a closer degree to the target thickness. In fact, Code C producing substrate 210C did not appear to provide a two layer structure at all, as the superabsorbent particles and the fibers intended to be provided in a second layer were found to distribute largely over a significant portion of the substrate 210C, including particularly near an upper surface 92 of the substrate 210C. FIG. 9C also depicts that fibers intended for the intake and distribution zones of the upper layer migrated towards the bottom surface 94 of the substrate 210C. Substrate 210C thus would not perform as well from an intake or distribution functionality without the proper fiber control. Therefore, use of a divider 36 including a z-directional divider 64 provides enhanced z-directional control of substrates 210A and 210B by providing higher levels of control of the relative thickness of the second layer 84, but also helps to provide a two layer 82, 84 structure to the substrate 210A, 210B whatsoever. This control over the fibers and/or particulates is surprising from the standpoint that the foam continues to be mobile and prone to mixing until it exits the headbox 16 and is completely dewatered.

The configuration of the divider 36 extending at least 50% of the length L of the headbox 16, or more preferably at least 60% of the length L of the headbox 16, was believed to provide enhanced control of the mixing of the first layer 82 and the second layer 84 of the substrate 210 at the interface 81 between layers 82, 84. Preferable substrates can include a second layer 84 that includes particulates (e.g., SAM particles) that has a relative thickness with less than 20% variance from the target relative thickness, or more preferably, a relative thickness that is less than 15% variance from the target relative thickness, or even more preferably, less than 10% variance from the target relative thickness. In some embodiments, preferable substrates can include a second layer 84 of a substrate 210A, 210B that can have particulates (e.g., SAM particles) and have a relative thickness less than 70% of the overall thickness of the structure, or more preferably, less than 60%, or in some embodiments, less than 55% of the absorbent structure. Thus, it can be seen that by providing a divider 36 creating a z-directional divider 64, a layer 84 can be produced to a relative thickness closer to a desired relative thickness, and therefore, can improve the overall purity of that layer 84 with respect to the resultant substrate.

Test Methods

Purity Gradient Test Method

The Purity Gradient Test Method can be used to measure the purity gradient of an interface 81 between two adjacent zones in a substrate, where the zones are in an external layer of the substrate. A digital camera, (such as a Sony DXC-5500), is used to take five digital images of each sample from a top-down view for purity gradient testing. The sample should be placed such that the layer including the zones and interface 81 being analyzed is facing up. The camera is set to black and white mode. The images are to be taken in an internal room with its lighting on. An additional light source is to be mounted on each side of the sample to be photographed. A Polaroid MP-4 Land Camera 44-02 stand (has ability to locate two lights on each side of sample) or similar set up is to be used to provide direct lighting on the surface of the sample. Care should be taken to ensure that no shadows are projected on the sample when taking the images with the digital camera.

The camera should capture images that encompass the interface 81 between adjacent zones for which the purity gradient is desired to evaluate, as well as at least a portion of each of such adjacent zone. For example, for samples described herein, the width of each image was approximately 14 centimeters (5.5 inches). A ruler is placed near the bottom of each image in order to set the length scale in later analysis. The five images taken for each sample should be taken at different machine directional locations along the interface 81. The camera is focused on the sample using the automatic focus of the digital camera. In black and white mode, the images have the ability to discern the difference between different fiber types via color differences in the fibers in the software analytical tool.

ImageJ software should be downloaded (such as from the National Institute of Health (NIH)—https://imagej.nih.gov/ij/) on to a computer. The five images for each sample are loaded into the ImageJ software. Once an image is opened in ImageJ, Auto BC is set on the image to normalize the images and the grayscale for the light fibers in one zone should be set to be the same as the light fibers in the other images, and likewise for the dark fibers (or particulates) of a different zone with dark fibers (or particulates) of that zone in the other images. The entire image is selected for analysis using the selection tool in the ImageJ software. Thus, the analyzed area and width is the same for each of the five images for each sample. The Plot Profile function in ImageJ software was used to obtain the gray scale as a function of distance across the image width. The Plot Profile function averages the gray scale for the selected area across the width of the image, and the average gray scale is plotted as a function of distance across the image.

Figure 11:
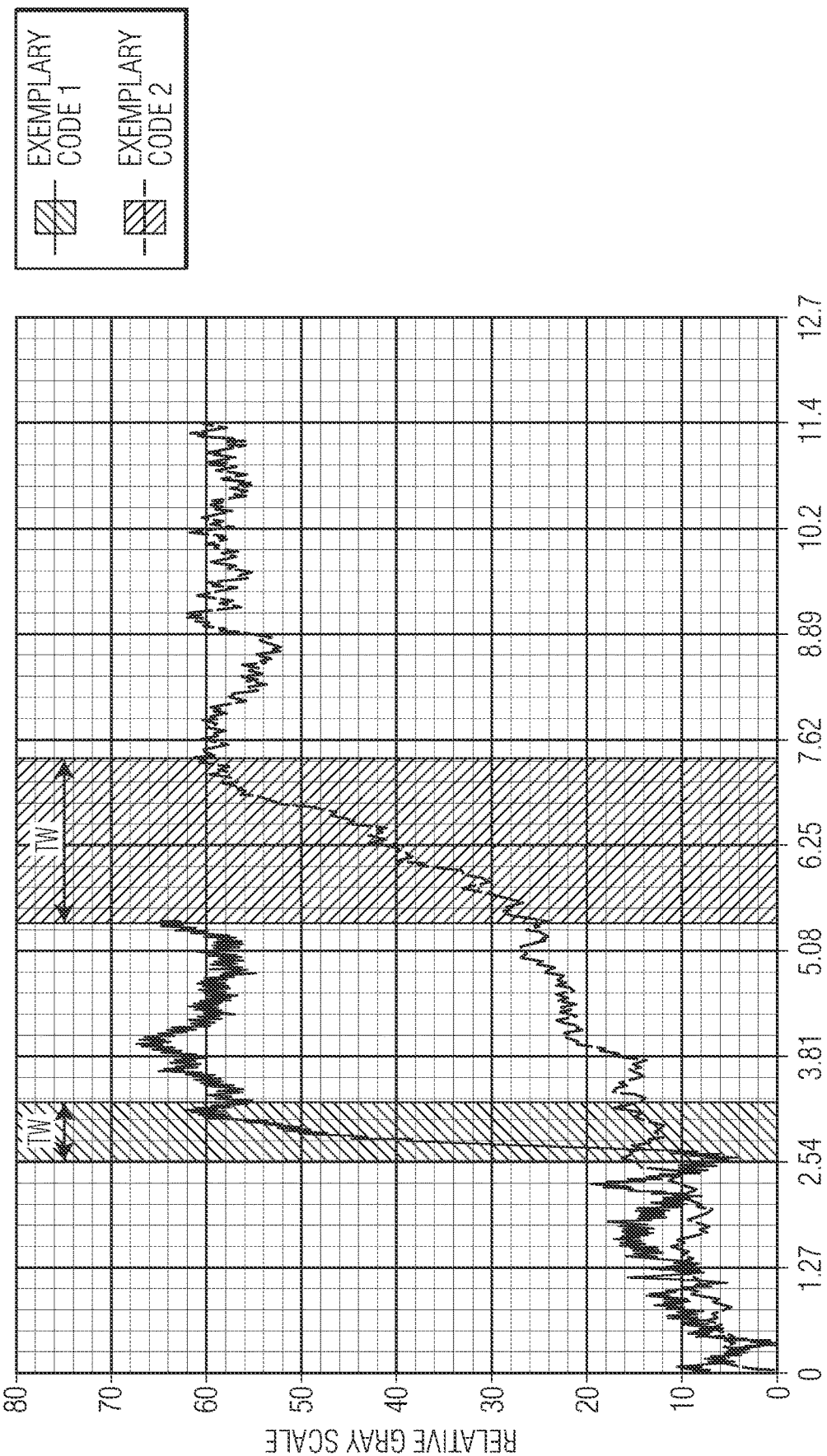
FIG. 11 is an exemplary analysis used in the Purity Gradient Test Method.

FIG. 11 illustrates ImageJ software Plot Profile function for two exemplary codes. As illustrated in FIG. 11, the transition width TW for each image is measured as the length of the interface determined from the gray scale plot based on where the gray scale began to increase from white and ending where it plateaued in the dark region. To account for the noise in the plot, the interface is taken to begin where the increase begins and continues to a grayscale of >30% over the starting or baseline level. For the zone surface image, a ruler was placed in each image in order to set the length scale as noted above. For purposes herein, the purity gradient transition width value for a sample interface 81 is the average transition width of the five images for each sample.

The transition slope is measured as the (change in grayscale)/(transition width), or the slope of a line connecting data points at the left and right sides of the transition zone as depicted in FIG. 11. The change in gray scale was the same for each image after the AutoBC normalization. For purposes herein, the purity gradient transition slope value for a sample interface 81 is the average transition slope of the five images for each sample.

Layer Relative Thickness Test Method

The Layer Relative Thickness Test Method is used to determine a particular layer thickness of a z-directional layer of a sample including two or more z-directional layers. For each sample substrate, seven cross-sectional images are taken. Each cross-sectional sample is imaged with conventional microCT equipment, such as Bruker Skyscan 1272, to provide an image such as those illustrated in FIGS. 9A-9C. The width of each sample for cross-sectional imaging is about 7 mm.

ImageJ software should be downloaded (such as from the National Institute of Health (NIH)—https://imagej.nih.gov/ij/) on to a computer. The seven images for each sample are loaded into the ImageJ software, converted to grayscale, and rotated ninety degrees, such that the interface 81 between separate layers 82, 84 is oriented in a generally vertical fashion. The image is made grayscale using the Make Binary function in ImageJ. Auto BC is set on the image to normalize the images and the grayscale for the light fibers in one layer should be set to be the same as the light fibers in the other images, and likewise for the dark fibers (or particles) of a different layer with dark fibers (or particles) of that layer in the other images.

Figure 12:
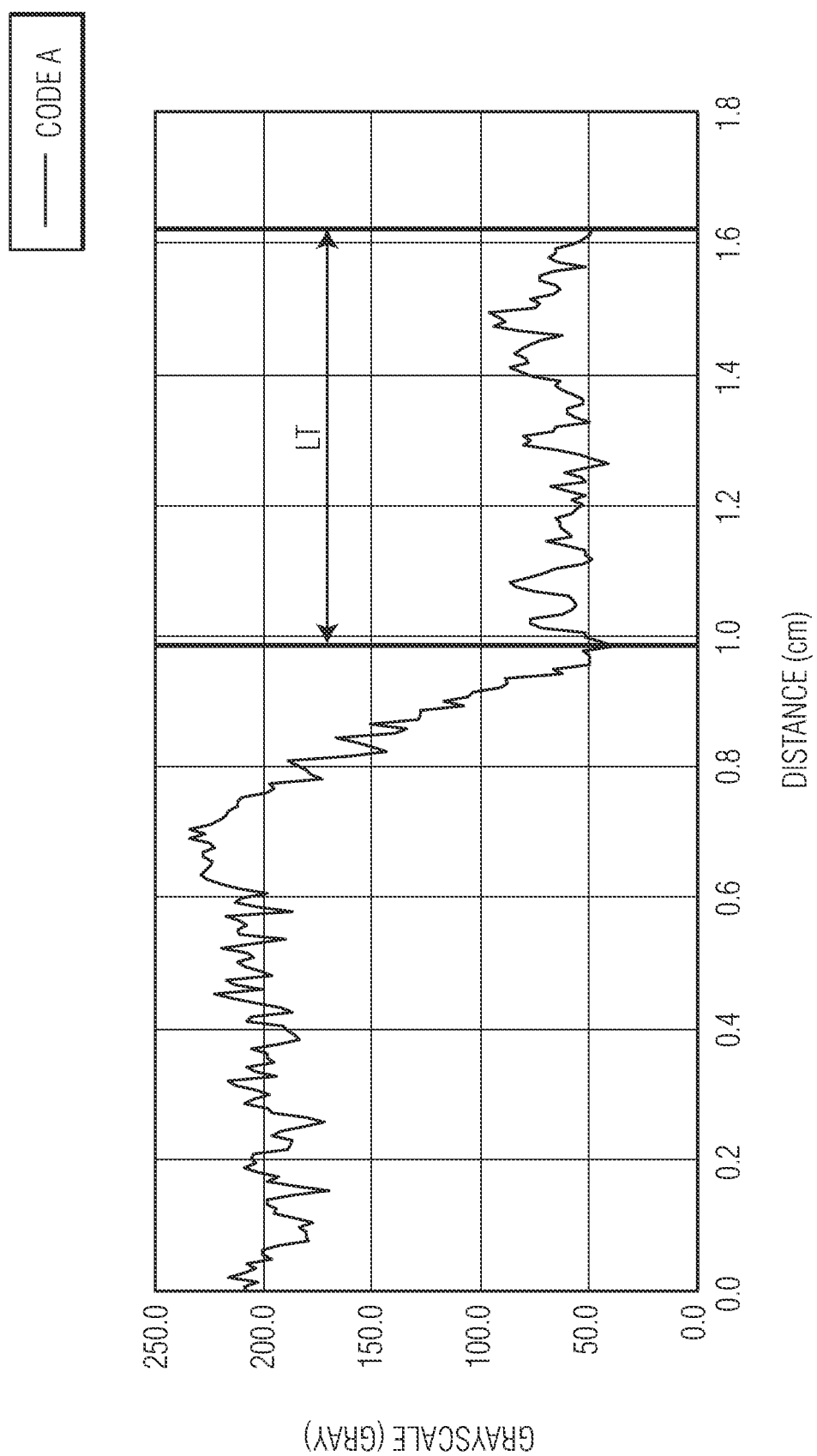
FIG. 12 is an exemplary analysis used in the Layer Relative Thickness Test Method.

As illustrated in FIG. 12, the layer thickness LT is measured by measuring the width of the layer where SAM particles are present using the grayscale plot from the plot profile function and setting an appropriate threshold to distinguish the region such as the mid-point of grayscale between the pure fiber region and the pure SAM region. The total thickness for a sample is the width of the area selected for the plot profile function. For purposes herein, a layer relative thickness for an image of a substrate is the measured layer thickness divided by the total thickness for that image. For purposes herein, a layer relative thickness percentage of the total thickness of a substrate is calculated by averaging the layer relative thickness for the seven images.

EMBODIMENTS

Embodiment 1: A substrate including a machine direction, a cross-direction, and a z-direction perpendicular to a plane defined by the machine direction and the cross-direction, the substrate comprising: a first layer, the first layer comprising: a first zone comprising a plurality of fibers; a second zone comprising a plurality of fibers, the second zone being offset from the first zone in the cross-direction; and an interface between the first zone and the second zone, the interface between the first zone and the second zone comprising at least some of the plurality of fibers of the first zone being mixed with at least some of the plurality of fibers of the second zone to provide a purity gradient with a transition width less than 3.8 cm as defined by a Purity Gradient Test Method as described herein.

Embodiment 2: The substrate of embodiment 1, wherein the purity gradient provides the transition width to be less than 3.0 cm.

Embodiment 3: The substrate of one of embodiments 1 or 2, wherein the purity gradient provides a transition slope greater than 28 gray/cm as defined by the Purity Gradient Test Method.

Embodiment 4: The substrate of embodiment 3, wherein the transition slope is greater than 40 gray/cm.

Embodiment 5: The substrate of any one of the preceding embodiments, wherein the first layer further comprises: a third zone, the third zone being offset from the first zone and the second zone in the cross-direction, the second zone being between the first zone and the third zone; and an interface between the second zone and the third zone, the interface between the second zone and the third zone comprising at least some of the plurality of fibers of the second zone being mixed with at least some of the plurality of fibers of the third zone to provide a purity gradient with at least one of a transition width less than 3.8 cm as defined by the Purity Gradient Test Method and a transition slope greater than 28 gray/cm as defined by a Purity Gradient Test Method.

Embodiment 6: The substrate of embodiment 5, further comprising: a second layer, the second layer being offset from the first layer in the z-direction.

Embodiment 7: The substrate of embodiment 6, wherein the second layer comprises superabsorbent material.

Embodiment 8: The substrate of one of embodiments 6 or 7, wherein the plurality of fibers in the first zone and the plurality of fibers in the third zone each comprise cellulosic fibers, and wherein the first zone and the third zone each comprise a binder.

Embodiment 9: The substrate of any one of embodiments 6-8, wherein the plurality of fibers in the second zone comprise synthetic fibers, and wherein the second zone further comprises a binder.

Embodiment 10: The substrate including a machine direction, a cross-direction, and a z-direction perpendicular to a plane defined by the machine direction and the cross-direction, the substrate comprising: a first layer, the first layer comprising: a first zone comprising a plurality of fibers; a second zone comprising a plurality of fibers, the second zone being offset from the first zone in the cross-direction; and an interface between the first zone and the second zone, the interface between the first zone and the second zone comprising at least some of the plurality of fibers of the first zone being mixed with at least some of the plurality of fibers of the second zone to provide a purity gradient with a transition slope greater than 28 gray/cm as defined by a Purity Gradient Test Method as described herein.

Embodiment 11: The substrate of embodiment 10, wherein the purity gradient provides the transition slope to be greater than 40 gray/cm.

Embodiment 12: The substrate of one of embodiments 10 or 11, wherein the first layer further comprises: a third zone, the third zone being offset from the first zone and the second zone in the cross-direction, the second zone being between the first zone and the third zone; and an interface between the second zone and the third zone, the interface between the second zone and the third zone comprising at least some of the plurality of fibers of the second zone being mixed with at least some of the plurality of fibers of the third zone to provide a purity gradient with at least one of a transition width less than 3.8 cm as defined by the Purity Gradient Test Method and a transition slope greater than 28 gray/cm as defined by the Purity Gradient Test Method.

Embodiment 13: The substrate of embodiment 12, further comprising: a second layer, the second layer being offset from the first layer in the z-direction.

Embodiment 14: The substrate of embodiment 13, wherein the second layer comprises superabsorbent material.

Embodiment 15: The substrate of any one of embodiments 12-14, wherein the plurality of fibers in the first zone and the plurality of fibers in the third zone each comprise cellulosic fibers, and wherein the first zone and the third zone each comprise a binder.

Embodiment 16: The substrate of embodiment 15, wherein the plurality of fibers in the second zone comprise synthetic fibers, and wherein the second zone further comprises a binder.

Embodiment 17: The substrate of claim 16, wherein the binder of the first zone, second zone, and third zone comprise binder fibers.

Embodiment 18: A substrate including a machine direction, a cross-direction, and a z-direction, the z-direction being perpendicular to a plane defined by the machine direction and the cross-direction, the substrate comprising: a first layer comprising: a first zone comprising a plurality of fibers; a second layer being offset from the first layer in the z-direction, the second layer comprising: a second zone comprising a plurality of superabsorbent material particles; and an interface between the first layer and the second layer, the interface between the first layer and the second layer comprising at least some of the plurality of fibers of the first zone of the first layer being mixed with at least some of the plurality of superabsorbent material particles of the second zone of the second layer; wherein the superabsorbent material particles of the second layer are controlled such that a relative thickness of the second layer is less than 70% of a total thickness of the substrate as measured by the Layer Relative Thickness Test as described herein.

Embodiment 19: The substrate of embodiment 18, wherein the plurality of fibers in the first zone comprise cellulosic fibers and binder fibers.

Embodiment 20: The substrate of any one of embodiments 18 or 19, wherein the relative thickness of the second layer is less than 60% of a total thickness of the substrate.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A substrate including a machine direction, a cross-direction, and a z-direction perpendicular to a plane defined by the machine direction and the cross-direction, the substrate comprising:
    a first layer, the first layer comprising:
        a first zone comprising a plurality of fibers;
        a second zone comprising a plurality of fibers, the second zone being offset from the first zone in the cross-direction; and
        an interface between the first zone and the second zone, the interface between the first zone and the second zone comprising at least some of the plurality of fibers of the first zone being mixed with at least some of the plurality of fibers of the second zone to provide a purity gradient with a transition width less than 3.8 cm as defined by a Purity Gradient Test Method.

2. The substrate of claim 1, wherein the purity gradient provides the transition width to be less than 3.0 cm.

3. The substrate of claim 1, wherein the purity gradient provides a transition slope greater than 28 gray/cm as defined by the Purity Gradient Test Method.

4. The substrate of claim 3, wherein the transition slope is greater than 40 gray/cm.

5. The substrate of claim 1, wherein the first layer further comprises:
    a third zone, the third zone being offset from the first zone and the second zone in the cross-direction, the second zone being between the first zone and the third zone; and
    an interface between the second zone and the third zone, the interface between the second zone and the third zone comprising at least some of the plurality of fibers of the second zone being mixed with at least some of the plurality of fibers of the third zone to provide a purity gradient with at least one of a transition width less than 3.8 cm as defined by the Purity Gradient Test Method and a transition slope greater than 28 gray/cm as defined by a Purity Gradient Test Method.

6. The substrate of claim 5, further comprising:
a second layer, the second layer being offset from the first layer in the z-direction.

7. The substrate of claim 6, wherein the second layer comprises superabsorbent material.

8. The substrate of claim 6, wherein the plurality of fibers in the first zone and the plurality of fibers in the third zone each comprise cellulosic fibers, and wherein the first zone and the third zone each comprise a binder.

9. The substrate of claim 6, wherein the plurality of fibers in the second zone comprise synthetic fibers, and wherein the second zone further comprises a binder.

10. A substrate including a machine direction, a cross-direction, and a z-direction perpendicular to a plane defined by the machine direction and the cross-direction, the substrate comprising:
a first layer, the first layer comprising:
a first zone comprising a plurality of fibers;
a second zone comprising a plurality of fibers, the second zone being offset from the first zone in the cross-direction; and
an interface between the first zone and the second zone, the interface between the first zone and the second zone comprising at least some of the plurality of fibers of the first zone being mixed with at least some of the plurality of fibers of the second zone to provide a purity gradient with a transition slope greater than 28 gray/cm as defined by a Purity Gradient Test Method.

11. The substrate of claim 10, wherein the purity gradient provides the transition slope to be greater than 40 gray/cm.

12. The substrate of claim 10, wherein the first layer further comprises:
a third zone, the third zone being offset from the first zone and the second zone in the cross-direction, the second zone being between the first zone and the third zone; and
an interface between the second zone and the third zone, the interface between the second zone and the third zone comprising at least some of the plurality of fibers of the second zone being mixed with at least some of the plurality of fibers of the third zone to provide a purity gradient with at least one of a transition width less than 3.8 cm as defined by the Purity Gradient Test Method and a transition slope greater than 28 gray/cm as defined by the Purity Gradient Test Method.

13. The substrate of claim 12, further comprising:
a second layer, the second layer being offset from the first layer in the z-direction.

14. The substrate of claim 13, wherein the second layer comprises superabsorbent material.

15. The substrate of claim 13, wherein the plurality of fibers in the first zone and the plurality of fibers in the third zone each comprise cellulosic fibers, and wherein the first zone and the third zone each comprise a binder.

16. The substrate of claim 15, wherein the plurality of fibers in the second zone comprise synthetic fibers, and wherein the second zone further comprises a binder.

17. The substrate of claim 16, wherein the binder of the first zone, second zone, and third zone comprise binder fibers.

18. A substrate including a machine direction, a cross-direction, and a z-direction, the z-direction being perpendicular to a plane defined by the machine direction and the cross-direction, the substrate comprising:
a first layer comprising:
a first zone comprising a plurality of fibers;
a second layer being offset from the first layer in the z-direction, the second layer comprising:
a second zone comprising a plurality of superabsorbent material particles; and
an interface between the first layer and the second layer, the interface between the first layer and the second layer comprising at least some of the plurality of fibers of the first zone of the first layer being mixed with at least some of the plurality of superabsorbent material particles of the second zone of the second layer;
wherein the superabsorbent material particles of the second layer are controlled such that a relative thickness of the second layer is less than 70% of a total thickness of the substrate as measured by the Layer Relative Thickness Test.

19. The substrate of claim 18, wherein the plurality of fibers in the first zone comprise cellulosic fibers and binder fibers.

20. The substrate of claim 18, wherein the relative thickness of the second layer is less than 60% of a total thickness of the substrate.

* * * * *